(12) United States Patent
Matheny et al.

(10) Patent No.: US 9,660,654 B2
(45) Date of Patent: May 23, 2017

(54) SYNCHRONIZATION OF NANOMECHANICAL OSCILLATORS

(71) Applicant: CALIFORNIA INSTITUTE OF TECHNOLOGY, Pasadena, CA (US)

(72) Inventors: Matthew Matheny, Diamond Bar, CA (US); Michael L. Roukes, Pasadena, CA (US); Michael C. Cross, Arroyo Grande, CA (US); Luis Guillermo Villanueva Torrijo, Los Angeles, CA (US); Rassul Karabalin, Los Angeles, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/063,905

(22) Filed: Oct. 25, 2013

(65) Prior Publication Data

US 2014/0176203 A1   Jun. 26, 2014

Related U.S. Application Data

(60) Provisional application No. 61/719,205, filed on Oct. 26, 2012.

(51) Int. Cl.
*H03L 7/00* (2006.01)
*G01N 29/11* (2006.01)
*H03B 5/30* (2006.01)

(52) U.S. Cl.
CPC ............... *H03L 7/00* (2013.01); *G01N 29/11* (2013.01); *H03B 5/30* (2013.01)

(58) Field of Classification Search
CPC ............... H03B 5/30; G01N 29/11; H03L 7/00
(Continued)

(56) References Cited

U.S. PATENT DOCUMENTS

2003/0033876 A1   2/2003   Roukes et al.
2005/0161749 A1   7/2005   Yang et al.
(Continued)

OTHER PUBLICATIONS

Acebrón, J. A., et al., "The Kuramoto model: A simple paradigm for synchronization phenomena", *Reviews of Modern Physics* 77, 137-185 (2005).

(Continued)

*Primary Examiner* — Arnold Kinkead
(74) *Attorney, Agent, or Firm* — The Marbury Law Group, PLLC

(57) ABSTRACT

Synchronization of oscillators based on anharmonic nanoelectromechanical resonators. Experimental implimentation allows for unprecedented observation and control of parameters governing the dynamics of synchronization. Close quantitative agreement is found between experimental data and theory describing reactively coupled Duffing resonators with fully saturated feedback gain. In the synchonized state, a significant reduction in the phase noise of the oscillators is demonstrated, which is key for applications such as sensors and clocks. Oscillator networks constructed from nanomechanical resonators form an important laboratory to commercialize and study synchronization—given their high-quality factors, small footprint, and ease of co-integration with modern electronic signal processing technologies. Networks can be made including one-, two-, and three-dimensional networks. Triangular and square lattices can be made.

36 Claims, 29 Drawing Sheets

(58) Field of Classification Search
USPC ............ 331/156, 46, 116 M, 2, 55; 327/156; 977/742; 73/579
See application file for complete search history.

(56) References Cited

U.S. PATENT DOCUMENTS

| | | | |
|---|---|---|---|
| 2006/0125576 A1* | 6/2006 | Ho et al. ........................ | 333/186 |
| 2007/0158553 A1 | 7/2007 | Roukes et al. | |
| 2008/0204152 A1 | 8/2008 | Feng et al. | |
| 2009/0261241 A1 | 10/2009 | Roukes et al. | |
| 2010/0074445 A1* | 3/2010 | Nefedov et al. ............... | 380/263 |
| 2010/0096709 A1 | 4/2010 | Roukes et al. | |
| 2010/0140066 A1* | 6/2010 | Feng et al. .................... | 200/181 |
| 2011/0260802 A1* | 10/2011 | Villanueva Torrijo et al. ............................. | 331/156 |
| 2012/0092083 A1* | 4/2012 | Nakamura .................... | 331/154 |
| 2012/0272742 A1 | 11/2012 | Andreucci et al. | |
| 2013/0043143 A1 | 2/2013 | Delapierre et al. | |
| 2013/0194048 A1* | 8/2013 | Feng et al. .................... | 331/154 |
| 2014/0142664 A1* | 5/2014 | Roukes et al. ................. | 607/88 |

OTHER PUBLICATIONS

Agrawal et al., "Observation of Locked Phase Dynamics and Enhanced Frequency Stability in Synchronized Micromechanical Oscillators", *Phys. Rev. Lett.*, 111, 084101; Aug. 23, 2013 (5 pages).
Adler, R., "A Study of Locking Phenomena in Oscillators", *Proceedings of the IRE*, 34, 351-357 (1946).
Arcamone, J. et al,. "A Compact and Low-Power CMOS Circuit for Fully Integrated NEMS Resonators", *Circuits and Systems II: Express Briefs, IEEE Transactions on Circuits and Systems*, 54, 377-381 (2007).
Aronson, D. G., et al. "Amplitude response of coupled oscillators", *Physica D: Nonlinear Phenomena* 41, 403-449, (1990).
Bargatin, I. et al. "Large-Scale Integration of Nanoelectromechanical Systems for Gas Sensing Applications", *Nano Letters* 12, 1269-1274 (2012).
Bazhenov, M. et al. "Model of Transient Oscillatory Synchronization in the Locust Antennal Lobe", *Neuron* 30, 553-567 (2001).
Blasius, B., et al. "Complex dynamics and phase synchronization in spatially extended ecological systems". *Nature* 399, 354-359, (1999).
Cross, M. C., et al., "Synchronization by reactive coupling and nonlinear frequency pulling", *Physical Review E* 73, 036205 (2006).
Cross, M.C., et al., "Synchronization by Nonlinear Frequency Pulling" *Phys. Rev. Lett.*, 93(22), 224101 (2004).
Demir, A., et al. "Phase noise in oscillators: a unifying theory and numerical methods for characterization", *IEEE Transactions on Circuits and Systems*, 47 (5), 655-674 (2007).
Ekinci, K. L., et al. "Balanced electronic detection of displacement in nanoelectromechanical systems", *Applied Physics Letters* 81, 2253-2255 (2002).
Geraci, A. A., et al., "Improved constraints on non-Newtonian forces at 10 microns". *Physical Review D* 78, 022002 (2008).
Heinrich, G., et al. "Collective Dynamics in Optomechanical Arrays". *Physical Review Letters* 107, 043603 (2011).
Holdeman, L. B. "Physics and Applications of the Josephson Effect"—Barone,A and Paterno,G. *American Scientist* 71, 306-306 (1983).
Holmes, C. A., et al. "Synchronization of many nanomechanical resonators coupled via a common cavity field". *Physical Review E* 85, 066203 (2012).
Kaka, S. et al. "Mutual phase-locking of microwave spin torque nano-oscillators". *Nature* 437, 389-392, (2005).
Karabalin, R. B. et al. Signal Amplification by Sensitive Control of Bifurcation Topology. *Physical Review Letters* 106, 094102 (2011).
Karabalin, R. B. et al. "Nonlinear dynamics and chaos in two coupled nanomechanical resonators". *Physical Review B* 79, 165309 (2009).
Karabalin, R. "*Nonlinear, coupled, and parametric nanoelectromechanical systems*", California Institute of Technology, (2008).
Li, M. et al. "Nanoelectromechanical Resonator Arrays for Ultrafast, Gas-Phase Chromatographic Chemical Analysis". *Nano Letters* 10, 3899-3903, (2010).
Lifshitz, R. et al. "Nonlinear Dynamics of Nanomechanical and Micromechanical Resonators", Reviews of Nonlinear Dynamics and Complexity, Wiley-VCH Verlag GmbH & Co. KGaA, pp. 1-51(2009).
Matheny et al., "Nonlinear Mode-Coupling in Nanomechanical Systems", *Nano Lett.*, 13(4), 1622-1626 (2013).
Mirollo, R. et al., "Synchronization of Pulse-Coupled Biological Oscillators". *SIAM Journal on Applied Mathematics* 50, 1645-1662, (1990).
Pikovsky, A., et al. "Synchronization : a universal concept in nonlinear sciences", Cambridge University Press, (2001). Table of Contents.
Schwab, K. C. et al., "Putting Mechanics into Quantum Mechanics". *Physics Today* 58, 36-42 (2005).
Shim, S. B., et al., "Synchronized Oscillation in Coupled Nanomechanical Oscillators", *Science* 316, 95-99 (2007).
Slavin, A. "Microwave sources: Spin-torque oscillators get in phase", *Nat Nano* 4, 479-480 (2009).
Topaj, D. et al., "Reversibility vs. synchronization in oscillator lattices". *Physica D: Nonlinear Phenomena* 170, 118-130, (2002).
Villanueva, L. G. et al. "A Nanoscale Parametric Feedback Oscillator" *Nano Letters* 11, 5054-5059, (2011).
Villanueva, L. G. et al. "Surpassing fundamental limits of oscillators using nonlinear resonators". *arXiv*: 1210.8075 (2012).
Zhang et al., "Synchronization of Micromechanical Oscillators Using Light", *Phys. Rev. Lett.*, 109, 233906(2012).

* cited by examiner

SYNCHRONIZATION OF NANOMECHANICAL OSCILLATORS

RELATED APPLICATIONS

The application claims priority to US provisional filing Ser. No. 61/719,205 filed Oct. 26, 2012, which is hereby incorporated by reference in its entirety.

FEDERAL FUNDING STATEMENT

This invention was made with government support under FA8650-10-1-7029 awarded by the USAF/ESC. The government has certain rights in the invention.

INTRODUCTION

Synchronization is a ubiquitous phenomenon both in the physical and the biological sciences. Synchronization of oscillators is an important topic, but experiemental studies on synchronized oscillators are limited. Synchronization also has many important commercial implications including for the commercialization of nanotechnology systems.

For example, nanomechanical systems can be improved through synchronization. To illustrate, NEMS oscillators have been exploited for a variety of applications, but arrays of these NEMS oscillators can suffer from statistical deviations. Arrays having large numbers of oscillators are important to increase sensitivity and provide better interfaces with the macroscopic world. The statistical deviations over a large number of arrays can lead to incoherence and eliminate advantages for the array.

A need exists to provide better, more coherent synchronized systems for NEMS oscillator arrays which move beyond the limits of theory and simulations.

SUMMARY

Embodiments described herein include systems, devices, and oscillator arrays with associated circuitry and computer control. Also provided are methods of making and using the same. Devices described herein can be used as research tools or in other applications described herein.

For example, one first embodiment provides for a device to provide synchronized oscillators comprising: a plurality of nanoelectromechanical resonators adapted to function as oscillators, each oscillator comprising an input port, an output port, and a port to control device resonance frequency; electronic circuitry electronically coupled to the oscillators and adapted so that the oscillators are synchronized with use of electronic feedback, wherein a signal from each oscillator is split into two different feedback loops. For a plurality of resonators or oscillators, these can be labeled as a first resonator, a second resonator, a third resonator, and so forth; and also a first oscillator, a second oscillator, a third oscillator, and so forth.

A second embodiment provides a device to provide synchronized oscillators comprising: a plurality of nanoelectromechanical resonators adapted to function as a plurality of oscillators, each oscillator comprising an input port and an output port; electronic circuitry electronically coupled to the oscillators and adapted to synchronize the plurality of oscillators by: controlling an anharmonicity of each of the plurality of oscillators; and controlling coupling between the plurality of oscillators. In one embodiment, an optional port to control device resonance frequency is present.

In a third embodiment, provided is a device to provide synchronized oscillators comprising: a plurality of coupled nanoelectromechanical resonators adapted to function as oscillators, each oscillator comprising at least one input coupling port, at least one output coupling port, and optionally at least one port to control device resonance frequency; and electronic circuitry coupled to the oscillators and adapted so that the oscillators are synchronized with the use of electronic control provided in a common coupling loop that couples respective output coupling ports and input coupling ports of adjacent ones of the oscillators. In one embodiment, the optional port to control device resonance frequency is present.

More particular embodiments are also described. In one embodiment, one of the two different feedback loops is an oscillator loop, and the other is a coupling loop. In one embodiment, one of the two different feedback loops is an oscillator loop, and the other is a coupling loop, wherein, for each oscillator, the coupling loop of the oscillator is coupled to the coupling loop of at least one other oscillator. In one embodiment, one of the two different feedback loops is an oscillator loop, and the other is a coupling loop, wherein the coupling loop of at least one oscillator is inductively coupled to the coupling loop of at least one other oscillator. In one embodiment, one of the two different feedback loops is an oscillator loop which is dissipative, and the other is a coupling loop which is reactive. In one embodiment, one of the two different feedback loops is an oscillator loop which is dissipative, and the other is a coupling loop which is reactive, wherein, for each oscillator, the oscillator loop is adapted to produce a nonlinear feedback signal in response to an oscillation amplitude signal; and the coupling loop is configured to produce signal that depends substantially linearly on a frequency detuning of the oscillator from at least one other coupled oscillator.

In one embodiment, one of the two different feedback loops is an oscillator loop, and the other is a coupling loop, wherein in the oscillator loop a signal is amplified with gain g and then sent through a saturating limiter. In one embodiment, one of the two different feedback loops is an oscillator loop, and in the oscillator loop a signal is amplified with gain g and then sent through a saturating limiter. In one embodiment, one of the two different feedback loops is an oscillator loop, and in the oscillator loop a signal is amplified with gain g and then sent through a saturating limiter and then to a voltage controlled attenuator after each limiter which sets a level of oscillation.

In one embodiment, one of the two different feedback loops for each oscillator is a coupling loop and comprises a common loop common to the two oscillators, wherein a signal is amplified so that a voltage controlled attenuator adjusts the signal level in the common loop, thereby setting the coupling strength. In one embodiment, a frequency difference is controlled by adjusting the stress induced in one of the resonators by a piezovoltage.

In one embodiment, the device provides for three parameter controls ($\Delta\omega, \alpha, \beta$) which are independent, wherein $\Delta\omega$ is the difference between resonant frequencies of the resonators, $\alpha$ is the amount of frequency pulling, and $\beta$ is the coupling strength. In one embodiment, the device provides for three parameter controls ($\Delta\omega, \alpha, \beta$) which are controlled by independent and external DC voltage sources, wherein $\Delta\omega$ is the difference between resonant frequencies of the resonators, $\alpha$ is the amount of frequency pulling, and $\beta$ is the coupling strength.

In one embodiment, the oscillators are coupled in a one-dimensional chain. In one embodiment, the oscillators are part of a multidimensional network. In one embodiment, the oscillators are part of a two-dimensional network. In one embodiment, the oscillators are part of a three-dimensional network. In one embodiment, the oscillators are part of a random network. In one embodiment, each oscillator is equally coupled to all other oscillators. In one embodiment, the oscillators are coupled through a transmission line. In one embodiment, the device further comprises a coupling bus adapted to provide selectable coupling of the oscillators.

In one embodiment, the device further comprising a coupling bus adapted to provide selectable coupling of the oscillators, wherein the selectable coupling is at least one of all-to-all coupling, nearest-neighbor coupling, or decaying coupling. In one embodiment, some but not all of the oscillators are coupled. In one embodiment, at least one attenuator is used between oscillators.

In one embodiment, the oscillators form part of an oscillator lattice. In one embodiment, the oscillators form part of a triangular lattice. In one embodiment, the oscillators form part of a hexagonal lattice. In one embodiment, the oscillators form part of a square lattice. In one embodiment, the device comprises two to 99 oscillators.

In one embodiment, the device comprises at least 100 oscillators. In one embodiment, the device comprises at least 10,000 oscillators. In one embodiment, the oscillators are part of a random network.

In one embodiment, each resonator is mounted on a separate oscillator circuit board, and further comprises a coupling bus in electrical communication with the oscillator circuit boards and is adapted to provide coupling between at least one pair of oscillators.

In one embodiment, the control of device resonance frequency is adapted to be carried out by modifying stress, by piezoelectric or thermal methods, or through a capacitive gate.

In one embodiment, the device is a frequency source. In one embodiment, the device comprises a sensor. In one embodiment, the device comprises an amplifier. In one embodiment, the device comprises a neural network.

In one embodiment, the electronic circuitry comprises, for each of the plurality of oscillators: an oscillator feedback loop configured to receive a signal from the output port and feed back a modified signal to the input port to adjust an anharmonicity of the oscillator.

In one embodiment, for each of the plurality of oscillators, the oscillator feedback loop is a dissipative feedback loop. In one embodiment, the anharmonicity comprises a frequency pulling. In one embodiment, each of the plurality of oscillators, the oscillator feedback loop provides a nonlinear response to the signal from the output port.

In one embodiment, the electronic circuitry comprises, for at least one pair of a first oscillator and a second oscillator from the plurality of oscillators: a coupling feedback loop configured to: receive an output signal from the output ports of the first and the second oscillator, feed back a modified signal to the input port of the first oscillator based on the output signals from the first oscillator and the second oscillator to control a coupling between the first oscillator and the second oscillator.

In one embodiment, the coupling feedback loop determines a frequency detuning between the first and second oscillators and the modified signal depends substantially linearly on the detuning. In one embodiment, the coupling feedback loop is substantially non-dissipative. In one embodiment, each of the plurality of resonators is mounted on an individual oscillator circuit board; the electronic circuitry comprises a coupling bus separate from but in electrical communication with each of the oscillator circuit boards and is adapted to provide coupling between the oscillators. In one embodiment, the coupling bus coupling bus adapted to provide selectable coupling of the oscillators. In one embodiment, the selectable coupling comprises at least one from the list consisting of: all-to-all coupling, nearest-neighbor coupling, and decaying coupling. In one embodiment, each oscillator has a respective fixed resonant frequency when uncoupled from the others in the plurality of oscillators. In one embodiment, the fixed resonant frequencies of the plurality of oscillators have a dispersion about a median frequency. In one embodiment, the electronic circuitry is adapted to synchronize the oscillators to substantially a single common frequency. In one embodiment, each of the plurality of oscillators comprises a control port adapted to receive a signal for tuning the uncoupled resonant frequency of the oscillator.

Other embodiments include a method of using the devices, oscillators, and resonators described herein, wherein the oscillators are used in a synchronized state. In one embodiment, the method further comprises synchronizing the oscillators; applying a stimulus to the oscillators that modifies the oscillation of the oscillators: combining output signals from the oscillators to generate a combined output signal indicative of the stimulus; and outputting the combined output signal. In one embodiment, the method step of applying the stimulus comprises causing a frequency shift in one or more of the oscillators in response to the stimulus. In one embodiment, the method step of combining output signals from the oscillators comprises coherently averaging the output signals from the oscillators such that the phase noise in the combined signal is inversely proportional to the number of oscillators.

Advantages for at least some embodiment described herein include, for example, excellent observation and control of parameters governing the dynamics of synchronization; and/or possible large scale integration; and/or close quantitative agreement between experiment and theory; and/or significant reduction in the phase noise of the oscillators in the synchronized state; and/or high-quality factors; and/or small footprint; and/or ease of co-integration with modern electronic signal processing technologies; and/or ability to have resonators not be in close proximity; and/or ability to systematically examine networks under different coupling, nonlinearity, and/or dispersion conditions. Another advantage for at least some embodiments is ability to study and model natural and biological systems, including neural systems.

BRIEF DESCRIPTION OF DRAWINGS

FIG. 1: Simplified circuit schematic used for testing equations 1-3. The NEMS resonators employed were selected to be as identical as possible. Each NEMS resonator (colored SEM micrograph) is embedded in two feedback loops: one is used for creating self-sustained oscillations in each resonator, and the other for implementing coupling between the two oscillators. In the feedback loops, the signal is amplified with gain g and then sent through a saturating limiter. The voltage controlled attenuators after each limiter (single heavy line boxes) in the feedback loop sets the level of oscillation, and constitutes a means to control the frequency pulling, a, in equation 3, shown by the dc control in green. In the coupling loop the signal is amplified so that a voltage controlled attenuator (double heavy line boxes) adjusts the signal level in the common loop, thereby setting the coupling strength, shown by the dc control in red. The frequency difference is controlled by adjusting the stress induced in the left resonator by the piezovoltage shown in blue.

FIG. 2: Synchronization in the limit of small coupling described by equations 5 and 6 with frequency pulling $\alpha=1.25$. a) Experimental data (points) are compared against theoretical predictions (lines) for the amplitudes of the two oscillators as the system moves through synchronization; the dependence upon detuning $\Delta\omega$ for a coupling of $\beta=0.068$ is shown. The synchronized region is shown by orange shading. b) Data and predictions for the frequency difference $\phi'$ for three different values of coupling. The set of data with the largest value of coupling $\beta=0.068$ corresponds to the amplitude data from the upper plot. Frequency locking is clearly shown where values $\phi'=0$ occur. This defines the synchronization regime, which increases in size as the coupling increases. Predictions of equation 5 and 6 are made by measuring the frequency pulling, coupling, and frequency detuning independently of the synchronization phenomenon. SR 0.012, SR 0.044, SR 0.068 denote the synchronized regimes (shaded regions) for the three couplings.

FIG. 3: Experimentally measured synchronization space as a function of coupling $\beta$ and frequency pulling $\alpha$ for three different detunings $\Delta\omega=0.6, 1, 2$. The basin of attraction, found from the time domain simulation of Equations 1-3, for an arbitrary initial phase is shown in blue (with white giving no synchronization and blue giving definite synchronization). All lines show boundaries with respective regions to the right of the line. The green solid line (REP) is the experimental boundary for the transition from unsynchronized to the synchronized state for repulsive coupling. The red solid line (ATT) is the experimental boundary for the transition from unsynchronized to the synchronized state for attractive coupling. The experimental synchronized state is defined as $\phi'<0.05$ (in units of the resonator width). The orange dashed line (LSA-1) depicts the theoretically-predicted (from a linear stability analysis) boundary for which at least one synchronized state (either in-phase or anti-phase, depending on coupling) is stable. Similarly, the purple dashed line (LSA-2) bounds the space for which both synchronized states are stable.

FIG. 4: Oscillator phase noise at 1 kHz offset from carrier frequency (blue and green spheres, left axis) and oscillator frequency difference (red diamonds, right axis) as coupling is increased. At the value of coupling $\beta=0.086$ the oscillator frequency difference goes to zero and the phase noise for both oscillators decreases by 3 dB, i.e., corresponding to reducing the phase noise by half. This effect is due to noise averaging noted by Reference 1.

FIG. 5: Driven response of the two devices. Note the similarity in frequency and quality factor.

FIG. 6: a) Oscillator magnitude squared (in mV$^2$) plotted against real frequency as the phase of oscillator feedback is varied. A Lorentzian fit to the data gives the maximum magnitude and central frequency of the Lorentzian. b) Frequency of oscillation as a function of the phase shifter voltage. The central frequency gives the correct phase shifter voltage.

FIG. 7: Different measurements to calibrate coupling. The green (blue) points are found using tuning data from oscillator 1 (2), and correspond to the left vertical axis. The red curve is found by measuring gain around the coupling loop; it corresponds to the right vertical axis.

FIG. 8: a) Raw data of sweeps of detuning under different coupling conditions (dashed lines $\beta=0$, solid lines $\beta=-0.28$), with each sweep taking minutes. The synchronization region appears when coupling is turned on. The two sweeps, taken hours apart, show that the NEMS device frequencies are drifting. b) Difference in frequency for the same sweeps. Straight lines are fit to the end sections of (b) in order to calibrate $\Delta\omega$ and correct for drifts.

FIG. 9: Single oscillator. The oscillator loop consists of a NEMS device, amplifier, coupling out, saturation (or auto gain control), attenuator, phase shift, and coupling in.

FIG. 10: Two direct coupled oscillators.

FIG. 11: Equivalent diagram for two directly coupled oscillators. The transformers, which could be replaced by stripline hybrid couplers invert the phase of the output signal from each oscillator by $\pi$.

FIG. 12: Equivalent diagram for two diffusively coupled oscillators. Coupling the top transformer primary to the outputs in this way provides a signal at the secondary equal to $X_{out,2}-X_{out,1}$. The bottom transformer feeds this signal in antiphase to each of the oscillator inputs.

FIG. 13: Coupling the oscillator to a transmission line in a bidirectional manner. Note that the controls of $\delta$, $\alpha$, $D_{adj}$ still exist, but are not shown.

FIG. 14: Topology for realizing bi-directional all-to-all coupling on a transmission line.

FIG. 15: Long range transmission line coupling created using attenuators between oscillator nodes. The attenuation can be externally controlled to create different levels of coupling, e.g., change the range (decay) of the coupling.

FIG. 16: Oscillator unit cell for triangular lattice.

FIG. 17: Regular triangular lattice where the number of connections per oscillator is 3.

FIG. 18: Triangular lattice where the number of connections per oscillator is 12.

FIG. 19: Oscillator unit cell for a square lattice.

FIG. 20: Square lattice of coupled oscillators.

FIG. 21: Oscillator unit cell for two overlapping coupling lattices. Oscillator unit cell fro implementing a square lattice with NN and NNN coupling. Inclusion of a programmable attenuator in the NNN input and output circuits allows for variable decay in the coupling strnength.

FIG. 22: Square array with two overlapping coupling lattices. When the coupling strengths are equal it becomes an octagonal array. Square array with NN and NNN coupling.

FIG. 23: Oscillator unit cell for a 3-d cubic lattice.

FIG. 24: Cubic 3-d lattice topology.

FIG. 25: Cubic 3-D lattice in planar circuitry.

FIG. 26: Topology for making general networks. The signal processing unit can change how oscillators are coupled. It is able to create adaptive connections to explore general dynamic networks.

FIG. 27: Simulation of 20 coupled oscillators with reactive coupling and frequency pulling. (a) The initial phase profile is given an overall 'winding number' of 1 with added noise (black). This evolves to a smooth winding number of 1 (red) as time progresses. (b) The dispersion of offset frequency for each oscillator shows that this behavior exists even in 'imperfect' oscillator rings. (c) The evolution in time of the ring (read right to left, top to bottom), where each sphere is a single oscillator and the black dashed line is zero amplitude. Clear smoothing of the noisy initial phase shows the robustness to phase imperfections. These ring rotations may provide a frequency source, whose noise has not yet been studied.

FIG. 28: An embodiment for a "mini-board which holds the NEMS oscillator.

FIG. 29: Two oscillators with frequency multiplexing. The dotted lines (routed on different board layers) are the parameter control lines, and the solid lines are the high frequency data lines.

DETAILED DESCRIPTION

Figure 1:
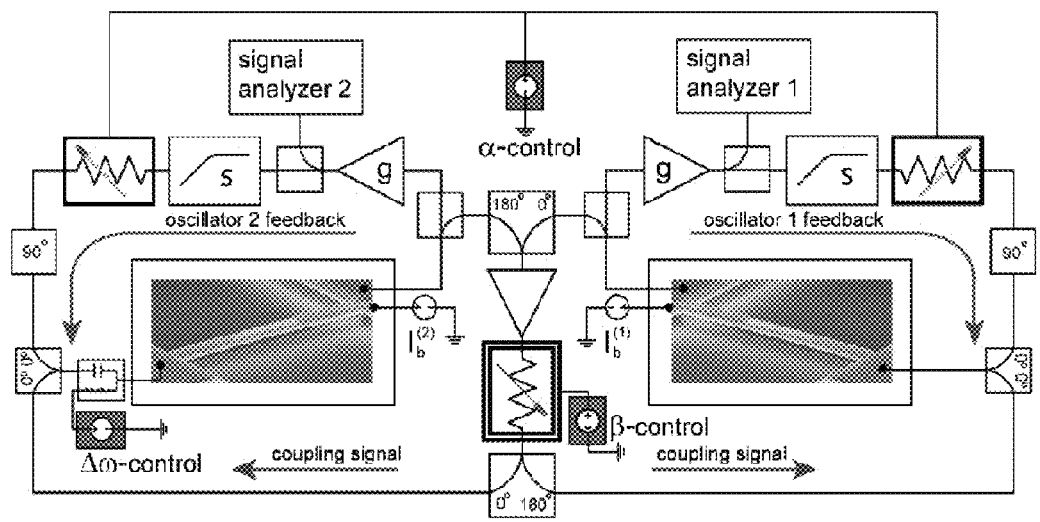
FIGS. 1-29 represent non-limiting embodiments of the invention and include color features which form part of the disclosure; the Applicants reserve the right to file color drawings to better illustrate the claimed inventions and various embodiments.

Part One: Synchronization of Two or More Oscillators (Main Text)

A list of cited references is provided hereinafter for Part One footnotes. No admission is made that any of these cited references are prior art.

Synchronization is a ubiquitous phenomenon both in the physical and biological sciences. It has been observed to occur over a wide range of scales—from the ecological[1], with oscillation periods of years, to the microscale[2], with oscillation periods of milliseconds. Although synchronization has been extensively studied theoretically[3-5], relatively few experimental systems have been realized that provide detailed insight into the underlying dynamics. Oscillators based on nanoelectromechanical systems (NEMS) can readily enable the resolution of such details, while providing many unique advantages for experimental studies of nonlinear dynamics[6,7,8].

For NEMS background and applications, see, for example, US Patent Publications 2008/0204152; 2011/0260802; and 2013/0194048 (Roukes et al.). See also 2013/0043143; 2012/0272742; 2010/0140066; 2010/0096709; 2009/0261241; 2007/0158553; 2005/0161749; 2003/0033876 (Roukes et al.), as well as Matheny et al., Nano Lett., 13(4), 1622-6 (2013); Villanueva, et al., Nano Lett., 11(11), 5054-9 (2011); and Cross et al., Phys. Rev. Lett., 2004, 93(22), 224101. See Shim et al., Science, 316, 95 (2007) and other references cited herein.

NEMS resonators can be HF, VHF, or UHF NEMS resonators and can operate in a range of 10-300 MHz with quality factors greater than 1,000. The NEMS resonators can be adapted as feedback oscillators to provide continuously controllable nodes for oscillator arrays. NEMS resonators can be adapted to function as oscillators. A variety of inorganic materials and elements can be used to form the resonators including silicon and single crystal silicon.

Herein, we demonstrate NEMS synchronization including, for example, synchronization of a pair of electronically-coupled NEMS oscillators, orchestrated through the inherent NEMS anharmonicity[9]. Our carefully calibrated experiments allow direct comparison to theoretical models and, in contrast to previous attempts[10,11], we obtain direct and unequivocal evidence of synchronization. While the working examples and experiments are impressively demonstrative, the full scope of the inventions described herein are not limited to the working examples and experiments.

These results described herein have particular relevance for, for example, NEMS sensors, which exhibit greatly enhanced sensitivities compared to their micro- and macroscale counterparts.[12] However, their decreased physical dimensions also engender increased thermal fluctuations— and this enhanced noise can overwhelm the smallest signals originating from measurements. By coherently averaging the response from synchronized NEMS arrays the superior response of nanoscale systems can be preserved, while maintaining the signal strengths and reduced fluctuations that are characteristic of macroscale systems. We demonstrate that synchronized averaging leads to a reduction in the phase noise of the oscillators that is useful for applications such as, for example, frequency-shift-based sensing and miniaturized frequency sources[13]. NEMS arrays offer realizable prospects for unprecedented synchronization experiments involving extremely large networks where each element can be independently addressed and fully characterized. For sake of clarity, the phrase "each oscillator" need not necessarily literally mean each, without exception, but can mean as understood by one skilled in the art as a majority of the oscillators in a system or device, such as for example, as least 70% of them, or at least 80% of them, or at least 90% of them. In principle, the synchronized oscillators described herein could be used with other types of oscillators and unsynchronized oscillators, even if not preferred. Small world networks, networks with community structures, and networks of networks can be made and used.

Synchronized networks fall into two separate classes based on the type of interactions between elements[3,14]. These interactions, the oscillator coupling, can be either dissipative or reactive (or a combination thereof). To date, most studies of synchronization have focused on dissipative coupling in a reduced single-variable description, i.e., the Kuramoto model[15]. In many systems with dissipative coupling, relative amplitude differences do not affect the synchronization, and are ignored. However, by contrast, many natural synchronized systems display reactive coupling[9], where the differences in individual oscillator amplitudes enable their synchronization. In the experiments reported herenbelow, we focus on reactive coupling and measure oscillator frequencies and amplitudes. Reactive coupling has been demonstrated in NEMS,[16,17] where it can be created straightforwardly through electrostatic or mechanical means. Previous theoretical work noted that possibly large arrays can synchronize through an interaction of anharmonicity inherent in NEMS devices with this reactive coupling[9]. This present work is an important milestone in the experimental demonstration of synchronization where unexpectedly both large scale behavior and individual elements can be simultaneously controlled and observed in detail.

Experimentally realizing large scale arrays of nanomechanical devices is now possible with current fabrication capabilities[13,18]; this yields systems where control over array parameters (such as frequency dispersion) is possible by design, and in some cases, in situ. Also, since these devices can be co-integrated with CMOS[19] electronics, experiments with short (about 1 ms) relaxation times[6] can be carried out with a large number of individually addressable elements that harness all the benefits of modern electronic signal processing. These attributes make NEMS oscillators unprecedented and apparently ideal candidates for synchronization studies and commercialization.

Additionally, NEMS arrays can provide exceptional performance as frequency-shift sensors or frequency sources, but their implementation can be challenging. For example, statistical deviations in batch fabrication inevitably lead to undesirable array dispersion[13]. However, upon synchronization, dispersive elements lock to a single frequency, with phase noise predicted within the simple dissipative model to be inversely proportional to the number of oscillators[3]. Attainment of this can mitigate the deleterious effects from an array's frequency dispersion. For example, the synchronization of spin-torque oscillators was recently demonstrated[20,21] with the goal of constructing nanoscale microwave frequency sources with appreciable power. It should be noted, however, that the studies on spin torque oscillators do not have the control of the complete set of parameters, as is shown here.

In addition, some theoretical modeling is provided. We describe our system with a set of equations similar to the model theoretically examined by Aronson et al.[22], except that here our system amplitude is not constrained by non-linear dissipation, but rather by amplifier saturation. We scale the amplitude in our equations by the level of saturation, and examine the system dynamics in "slow" time, $T \sim Q^* t^* \omega_o$, where Q is the quality factor of the resonators and $\omega_o$ the linear resonance frequency of the NEMS device when under driven excitation, and t is the real time in seconds. In the slow time dynamics, feedback loop time delays are represented by a phase shift. The resulting equations for the amplitudes $a_{1,2}$ for each oscillator and phase difference $\phi$ between them are $$a_1' \equiv \frac{da_1}{dT} = -\frac{a_1}{2} + \frac{1}{2} - \frac{\beta}{2}a_2\sin\varphi, \quad (1)$$

$$a_2' \equiv \frac{da_2}{dT} = -\frac{a_2}{2} + \frac{1}{2} + \frac{\beta}{2}a_1\sin\varphi, \quad (2)$$

$$\varphi' \equiv \frac{d\varphi}{dT} = \Delta\omega - (a_1^2 - a_2^2)\left(\alpha - \frac{\beta}{2a_1 a_2}\cos\varphi\right), \quad (3)$$

(see Supplementary Information section I). Here $\Delta\omega$ is the difference between the resonant frequencies of the devices, $\alpha$ is the measure of the amount of frequency pulling (which is the increase in frequency proportional to the square of the amplitude), and $\beta$ is the coupling strength. The parameters $\Delta\omega$, $\alpha$, and $\beta$, which we call the synchronization parameters, set the dynamics of the system: the stable fixed points of equations 1-3, for example, yield synchronized states. These parameters are expressed in units of the device's resonance line width, $\omega_0/Q$. For example, $\Delta\omega=1$ corresponds to a resonator frequency difference of 1 line width. Note when the coupling term is not present ($\beta=0$), we obtain a fixed point for equations 1-3 such that $a_1=a_2=1$ and $\phi'=\Delta\omega$. Therefore, by measurement of the uncoupled oscillator amplitudes and frequency differences we can calibrate the frequency pulling $\alpha$, and detuning $\Delta\omega$.

In order to construct an exemplary experiment with independent control of the synchronization parameters, we use the setup shown in FIG. 1. In this exemplary embodiment, the NEMS devices are two piezoelectrically actuated, piezoresistively detected,[23] doubly-clamped beams 10 μm long, 210 nm thick, and 400 nm wide. Other NEMS resonators can be used with different design, materials, and dimensions. The signal from each beam is split into two different feedback loops. One feedback loop sets the level of oscillations (the oscillator loop), and the other loop sets the coupling (the coupling loop). In the oscillator loop, the signal is strongly amplified (gain stage, g) into a diode limiter (saturation stage, s) in order to ensure the feedback signal to the beam is of constant magnitude[24]. Therefore, the feedback signal is a strongly nonlinear function of the device displacement. On the other hand, the coupling loop is kept linear; the feedback is directly proportional to the displacement over the full range of experimental values. For the oscillator loop, the signal is fed back in phase with the beam's velocity. For the coupling loop, this signal is fed into the beams in phase with the displacement. This causes the coupling branch to be reactive and the oscillator loop to be dissipative.

Other than the phase shifters, the system can further comprise, for example, transistor amplifiers, saturation diodes, and direction couplers (capacitors). Here we use adjustable attenuators, however these can be implemented with adjustable amplifiers. We note that if we measure the piezoelectric response in addition to the piezoresistive response, we are able to directly capture both the in-phase and out-of-phase response of the oscillators, without the need of additional phase shifters. This solution finds the most application when the feedback delay is small compared to the period of the signal when all the components are integrated on chip.

It is important to note that the three parameter controls ($\Delta\omega$, $\alpha$, $\beta$) are independent. This makes the experimental data easier to process, and helps clearly identify which modified parameter induces synchronization. For more details on the individual circuits and calibration of synchronization parameters see the Supplementary Information, Section II.

We begin further description by looking at the small coupling limit, with the coupling less than a tenth of the resonator width, where experimental data can be compared to analytical predictions. In that case, the amplitudes of the two oscillators stay near unity (the fixed points of equations 1,2 give $a_{1,2} \approx 1 \pm \beta \sin\phi$). In this limit, equation 3 assumes the form of the Adler equation[25]

$$\phi' = \Delta\omega + 4\alpha\beta \sin\phi. \quad (4)$$

Note that even though this equation is of the same form as Adler's study of injection locking, our equation is describing the mutual synchronization of two oscillators (see Supplementary Information). When the oscillators are unsynchronized, its solution can expressed in terms of the oscillator frequency difference $$\phi' = \sqrt{\Delta\omega^2 - (4\alpha\beta)^2}. \quad (5)$$

Equations 4 and 5 mimic an overdamped Josephson junction using the RCSJ model[26]. The oscillator phase difference $\phi$ corresponds to the phase difference across the Josephson junction, the detuning $\Delta\omega$ to the injected DC current (normalized to the ratio of the junction's normal state resistance and a flux quantum), and the frequency pulling-coupling term $4\alpha\beta$ to the critical current (again normalized to the ratio of the junction's normal state resistance and a flux quantum). However, unlike the critical current which is fixed by junction geometry in the RCSJ model, here we can experimentally control both frequency pulling and coupling independently.

Figure 2:
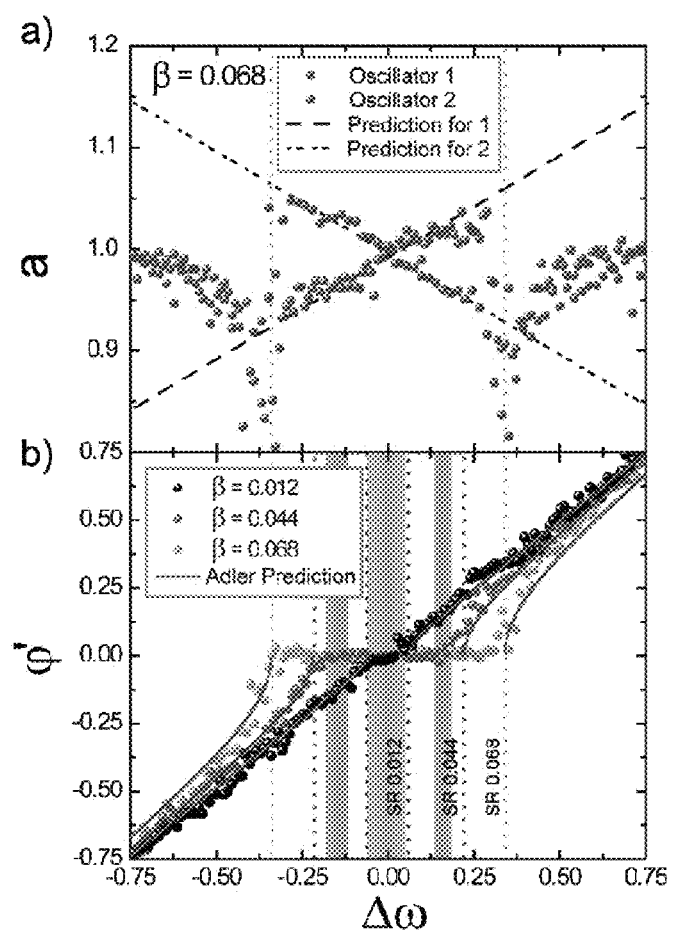

In FIG. 2, we compare the analytical predictions of equations 5 and 6 with the experimental data for the amplitudes and frequency difference as the detuning is swept, with fixed value of frequency pulling $\alpha=1.25$. In FIG. 2 $\phi'$ is the oscillator frequency difference in units of the resonance width. In the synchronization regime, as the amplitudes stay near unity, a linear relationship between the oscillation amplitudes and the frequency difference is found from equation 4 for, $$\frac{\Delta a_{1,2}}{a_{1,2}} = \pm \frac{\Delta\omega}{4\alpha}, \quad (6)$$

where 1,2 corresponds to +,-, respectively. The plots clearly show synchronization between the two coupled oscillators. The agreement between theoretical predictions, given by the Adler equation, and the experimental data is remarkable and unexpected. Note that upon synchronization, the oscillator amplitudes change in order to adjust the oscillator frequencies. This shows that the frequency pulling is crucial to the synchronization for reactive coupling.

Figure 3:
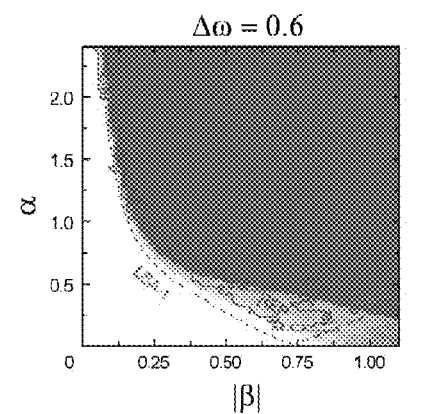
Figure 3:
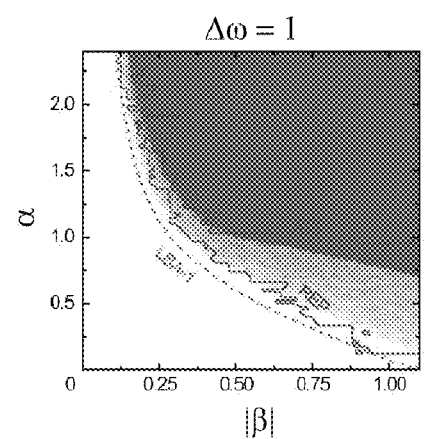
Figure 3:
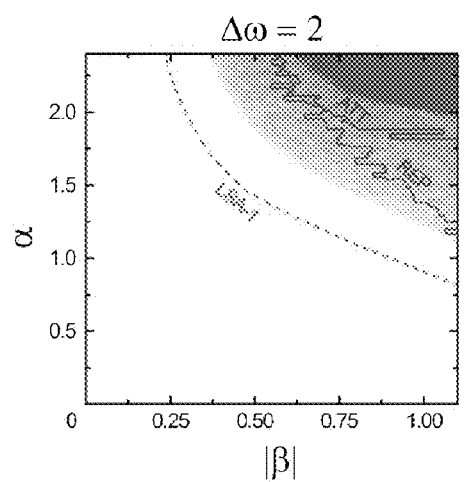

In addition to control of the detuning through a wide range of values (shown in FIG. 2), we are able to modify both the frequency pulling and coupling, to study the parameter space for synchronization. FIG. 3 shows the synchronization parameter space for three levels of fixed detuning ($\Delta\omega$=0.6, 1,2) as coupling and frequency pulling $\alpha$ are varied. The red border is the data with attractive coupling ($\beta$<0 in equations 1-3) and green with repulsive coupling ($\beta$>0 in equations 1-3). These lines represent the boundaries of the transition between synchronized and unsynchronized states when sweeping to higher values of coupling, i.e., from left to right in FIG. 3. This transition is defined by a change to a measured oscillator frequency difference $\phi'$<0.05.

In general, analytical solutions to equations 1-3 cannot be found. Therefore, we perform two numerical studies and compare them to the experiment. We perform a linear stability analysis (LSA) of equations 1-3 with the orange and purple dashed lines in FIG. 3 showing the stability boundaries. We also perform a time domain simulation of equations 1-3, using initial conditions of amplitudes fixed at 1 and random phases. This time domain simulation gives us a basin of attraction for stabilizing in either unsynchronized or synchronized states. For each value for the parameters plotted in FIG. 3, we run 100 such simulations and average a "synchronization value" between 0 for unsynchronized and 1 for synchronized. The average value of these simulations are represented by the white for unsynchronized for every random phase, or blue synchronized for every random phase. For simulations with intermediate values between 0 and 1, we mix blue and white on a linear gradient.

We can see a clear distinction between the sets of experimental data corresponding to attractive and repulsive coupling (red and green lines). However, Equations 1-3 are completely symmetric upon exchange of $\beta \rightarrow -\beta$, since synchronization will occur for $\phi \rightarrow \phi + \pi$. The numerical time-domain simulation shows correspondence to the experimental data, indicating that the initial phase difference of the oscillators is not completely random. The lightest blue basins of attraction are those where the initial phase must be close to $\phi_0 = \pi$ in order to synchronize. More initial phase conditions will synchronize as the basins transition from light to dark. When totally dark even initial phase conditions near $\phi_0 = 0$ will synchronize. Thus the sign of coupling tends to bias the experiment to different initial phase conditions.

In the set of data with largest detuning, $\Delta\omega$=2, the experiment shows somewhat larger departure from theoretical predictions. We observe that at large detunings, asymmetries in saturation level or discrepancies in quality factor between the two oscillators tend to create larger disagreement between theory and experiment. This is due to the large coupling necessary in order to synchronize the oscillators, which magnifies the nonlinear behavior (and thus asymmetry) of the system. However, the close agreement of FIGS. 2 and 3 show the generality and accuracy of our approach.

Figure 4:
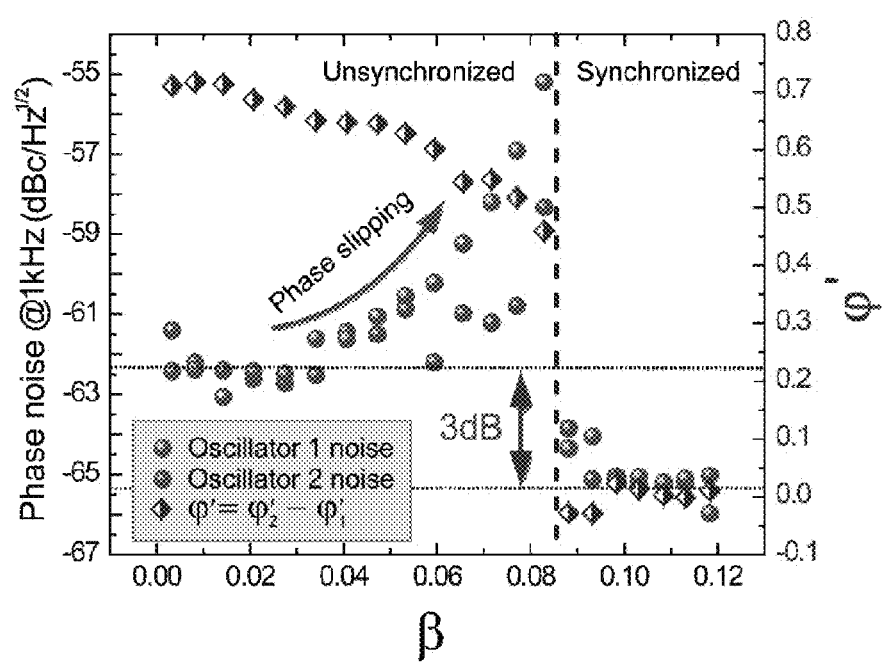

Finally, we explore the effect of synchronization on the phase noise. In FIG. 4, the green and blue spheres are the phase noise at 1 kHz offset from the carrier frequency (a key figure-of-merit for the frequency source community[27]) plotted as a function of coupling for oscillators 1 and 2, respectively. For more information on FIG. 4, please see the Supplementary Information Section III. The red diamonds show the oscillator frequency difference $\phi'$ for comparison. As coupling is increased the phase noise at this offset initially increases (due to phase slipping between the oscillators) and then suddenly drops to 3 dB below the uncoupled noise level. The plot of the oscillator frequency difference indicates the phase noise reduction occurs at the onset of synchronization. This corresponds to a phase noise reduction by factor of two, as predicted by theoretical estimates[3]. If acted upon by the same stimulus, this oscillator array would show an improvement in signal-to-noise. This would be useful for measurement of weak global quantities, such as, for example, gravitational fields[28] or gas environments[18].

In summary, our demonstration of the synchronization of two reactively coupled anharmonic NEMS oscillators shows excellent agreement with analytical and numerical modeling. We track not only the frequency difference, but also the individual amplitudes, important for a full multivariable description of the synchronization. These results highlight the importance of the oscillator amplitudes in synchronization for reactive coupling. This work highlights the importance and advantages of nonlinear dynamics experiments at the intermediate scale of discretization: full control of individual elements and tracking of large arrays is now possible. All of the components in these experiments can be realized in CMOS, implying that very-large-scale networks can be built using the precise technology of present-day semiconductor nanoelectronics and electronically tested with co-integrated state-of-the-art signal processing capabilities. The flexibility of this system permits creation of dissipative or reactive coupling in arbitrarly complex or completely random networks. Our experimental demonstration of reduced phase noise in the synchronized state enables the detection of very weak phenomena using coupled nanoscale sensor arrays.

Additional embodiments are provided in the following, non-limiting working examples.

WORKING EXAMPLES

Experimental Methods: Device fabrication has been previously described by Villanueva et al[23]. All measurements were taken at a pressure of less than 100 mT through a balanced bridge technique (not pictured in the figure)[29] in order to reduce the effect of parasitic capacitances[24]. All three synchronization parameters are modified by external and independent DC voltage sources. The coupling strength can be controlled by adjusting the feedback gain in the coupling loop. We amplify and tune (using the red DC control voltage box in FIG. 1) a voltage controlled attenuator (double-line box in FIG. 1) in order to modify this coupling feedback gain. The frequency difference between the two oscillators can be linearly controlled by inducing stress in one of the beams by a DC piezovoltage, as shown by the blue box in FIG. 1. The frequency pulling can be adjusted by varying the absolute oscillator amplitudes (keeping the relative amplitudes fixed to ensure that Equations 1-3 remain valid) through the use of the voltage controlled attenuators (single-line dark box controlled by green DC voltage). The amplifiers used in the setup were tested at each stage to ensure linearity of signal transfer. For more information see Supplementary Information section II. All data (except for phase noise) are taken by two separate spectrum analyzers so that amplitude and frequency can be measured independently for the two oscillators. Phase noise is measured on a single spectrum analyzer with a phase noise module, with the input switched for either oscillator. Simulations (FIG. 3) of the basins of attraction were carried out in Matlab, and the linear stability analysis was carried out in Mathematica.

REFERENCES CITED

1 Blasius, B., Huppert, A. & Stone, L. Complex dynamics and phase synchronization in spatially extended ecological systems. *Nature* 399, 354-359, doi:http://www.nature.com/nature/journal/v399/n6734/suppinfo/399354a0_S1.html (1999).
2 Bazhenov, M. et al. Model of Transient Oscillatory Synchronization in the Locust Antennal Lobe. *Neuron* 30, 553-567, doi:10.1016/s0896-6273(01)00284-7 (2001).
3 Pikovsky, A., Rosenblum, M. & Kurths, J. *Synchronization: a universal concept in nonlinear sciences*. (Cambridge University Press, 2001).
4 Tyrrell, A., Auer, G. & Bettstetter, C. in *Bio-Inspired Models of Network, Information and Computing Systems*, 2006. 1st. 1-7.
5 Mirollo, R. & Strogatz, S. Synchronization of Pulse-Coupled Biological Oscillators. *SIAM Journal on Applied Mathematics* 50, 1645-1662, doi:doi:10.1137/0150098 (1990).
6 Lifshitz, R. & Cross, M. C. *Nonlinear Dynamics of Nanomechanical and Micromechanical Resonators*. (Wiley-VCH Verlag GmbH & Co. KGaA, 2009).
7 Heinrich, G., Ludwig, M., Qian, J., Kubala, B. & Marquardt, F. Collective Dynamics in Optomechanical Arrays. *Physical Review Letters* 107, 043603 (2011).
8 Holmes, C. A., Meaney, C. P. & Milburn, G. J. Synchronization of many nanomechanical resonators coupled via a common cavity field. *Physical Review E* 85, 066203 (2012).
9 Cross, M. C., Lifshitz, R. & Zumdieck, A. Synchronization by reactive coupling and nonlinear frequency pulling. *Physical Review E* 73, doi:10.1103/PhysRevE.73.036205 (2006).
10 Zhang, M. et al. Synchronization of Micromechanical Oscillators Using Light. arXiv:1112.3636 (2011).
11 Shim, S. B., Imboden, M. & Mohanty, P. Synchronized Oscillation in Coupled Nanomechanical Oscillators. *Science* 316, 95-99, doi:10.1126/science.1137307 (2007).
12 Schwab, K. C. & Roukes, M. L. Putting Mechanics into Quantum Mechanics. *Physics Today* 58, 36-42 (2005).
13 Bargatin, I. et al. Large-Scale Integration of Nanoelectromechanical Systems for Gas Sensing Applications. *Nano Letters* 12, 1269-1274, doi:10.1021/nl2037479 (2012).
14 Topaj, D. & Pikovsky, A. Reversibility vs. synchronization in oscillator lattices. *Physica D: Nonlinear Phenomena* 170, 118-130, doi:10.1016/s0167-2789(02)00536-5 (2002).
15 Acebrón, J. A., Bonilla, L. L., Perez Vicente, C. J., Ritort, F. & Spigler, R. The Kuramoto model: A simple paradigm for synchronization phenomena. *Reviews of Modern Physics* 77, 137-185 (2005).
16 Karabalin, R. B. et al. Signal Amplification by Sensitive Control of Bifurcation Topology. *Physical Review Letters* 106, 094102 (2011).
17 Karabalin, R. B., Cross, M. C. & Roukes, M. L. Nonlinear dynamics and chaos in two coupled nanomechanical resonators. *Physical Review B* 79, 165309 (2009).
18 Li, M. et al. Nanoelectromechanical Resonator Arrays for Ultrafast, Gas-Phase Chromatographic Chemical Analysis. *Nano Letters* 10, 3899-3903, doi:10.1021/nl101586s (2010).
19 Arcamone, J. et al. A Compact and Low-Power CMOS Circuit for Fully Integrated NEMS Resonators. *Circuits and Systems II: Express Briefs, IEEE Transactions on* 54, 377-381, doi:10.1109/tcsii.2007.892228 (2007).
20 Slavin, A. Microwave sources: Spin-torque oscillators get in phase. *Nat Nano* 4, 479-480 (2009).
21 Kaka, S. et al. Mutual phase-locking of microwave spin torque nano-oscillators. *Nature* 437, 389-392, doi:10.1038/nature04035 (2005).
22 Aronson, D. G., Ermentrout, G. B. & Kopell, N. Amplitude response of coupled oscillators. *Physica D: Nonlinear Phenomena* 41, 403-449, doi:10.1016/0167-2789(90)90007-c (1990).
23 Villanueva, L. G. et al. A Nanoscale Parametric Feedback Oscillator. *Nano Letters* 11, 5054-5059, doi:10.1021/nl2031162 (2011).
24 Villanueva, L. G. et al. Surpassing fundamental limits of oscillators using nonlinear resonators. arXiv: 1210.8075 (2012).
25 Adler, R. A Study of Locking Phenomena in Oscillators. *Proceedings of the IRE* 34, 351-357 (1946).
26 Holdeman, L. B. Physics and Applications of the Josephson Effect—Barone,a, Paterno,G. *American Scientist* 71, 306-306 (1983).
27 Demir, A., Mehrotra, A. & Roychowdhury, J. Phase noise in oscillators: a unifying theory and numerical methods for characterization. *Circuits and Systems I: Fundamental Theory and Applications, IEEE Transactions on* 47, 655-674 (2000).
28 Geraci, A. A., Smullin, S. J., Weld, D. M., Chiaverini, J. & Kapitulnik, A. Improved constraints on non-Newtonian forces at 10 microns. *Physical Review D* 78, 022002 (2008).
29 Ekinci, K. L., Yang, Y. T., Huang, X. M. H. & Roukes, M. L. Balanced electronic detection of displacement in nanoelectromechanical systems. *Applied Physics Letters* 81, 2253-2255 (2002).

Part One: Supplementary Information

A list of cited references for the Supplemental Information Section footnotes is provided hereinafter. No admission is made that any reference cited in prior art.

I. Theoretical Derivation of Synchronization Equations for Two Anharmonic Oscillators We start with the slow time equation for two oscillators with two feedback[1,2] terms: one which is common to both oscillators ($f_c$), and one that affects the corresponding oscillator only ($f_i$, i=1,2). These are $$\frac{d\tilde{A}_1}{dT} - i\left(\frac{\delta_1}{2} + \lambda_{11}|\tilde{A}_1|^2\right)\tilde{A}_1 + \frac{\tilde{A}_1}{2} = f_1(\tilde{A}_1) + f_c(\tilde{A}_1, \tilde{A}_2), \quad (S.I.1)$$

and $$\frac{d\tilde{A}_2}{dT} - i\left(\frac{\delta_2}{2} + \lambda_{22}|\tilde{A}_2|^2\right)\tilde{A}_2 + \frac{\tilde{A}_2}{2} = f_2(\tilde{A}_2) + f_c(\tilde{A}_2, \tilde{A}_1) \quad (S.I.2)$$

where $$\delta_{1,2} = Q\left(\frac{\omega_{1,2}^2}{\omega_0^2} - 1\right)$$

defines the offset of the natural resonance frequency of each NEMS device $\omega_{1,2}$ to a nearby frequency, $\omega_0$, $\tilde{A}=ae^{i\phi}$ is the complex slow time oscillator displacement, and the nonlinear coefficient $\lambda$ is the relationship of the device displacement to the relative change in the NEMS resonance frequency (there is a factor of 3/8 that has been folded into this constant with respect to references 1 and 2). The terms $f_{1,2}$ and $f_c$ are the "oscillator feedback" and "coupling signal" in FIG. 1, respectively. For a saturated oscillator feedback with linear, reactive, diffusive coupling these equations become $$\frac{d\tilde{A}_1}{dT} - i\left(\frac{\delta_1}{2} + \lambda_{11}|\tilde{A}_1|^2\right)\tilde{A}_1 + \frac{\tilde{A}_1}{2} = \frac{s}{2}e^{i\varphi_1} + i\frac{\beta}{2}(\tilde{A}_2 - \tilde{A}_1), \quad (S.I.3)$$

and $$\frac{d\tilde{A}_2}{dT} - i\left(\frac{\delta_2}{2} + \lambda_{22}|\tilde{A}_2|^2\right)\tilde{A}_2 + \frac{\tilde{A}_2}{2} = \frac{s}{2}e^{i\varphi_2} + i\frac{\beta}{2}(\tilde{A}_1 - \tilde{A}_2), \quad (S.I.4)$$

where s is the level of the saturation, and β is the (real-valued) strength of the coupling.

The magnitude of oscillation can be scaled by the saturation s ($\tilde{A}=A*s$), which yields $$\frac{dA_1}{dT} - i\left(\frac{\delta_1}{2} + \lambda_{11}s^2|A_1|^2\right)A_1 + \frac{A_1}{2} = \frac{1}{2}e^{i\varphi_1} + i\frac{\beta}{2}(A_2 - A_1), \quad (S.I.5)$$

and $$\frac{dA_2}{dT} - i\left(\frac{\delta_2}{2} + \lambda_{22}s^2|A_2|^2\right)A_2 + \frac{A_2}{2} = \frac{1}{2}e^{i\varphi_2} + i\frac{\beta}{2}(A_1 - A_2). \quad (S.I.6)$$

We combine the terms $\lambda_{11}s^2$ into a single term a, which is the nonlinear frequency pulling[3].

Equations S.I.5 and S.I.6 can be separated into magnitude and phase, $$\frac{da_1}{dT} = -\frac{a_1}{2} + \frac{1}{2} + \text{Re}\left(i\frac{\beta}{2}(a_2 e^{i(\varphi_2-\varphi_1)} - a_1)\right), \quad (S.I.7)$$

$$\frac{da_2}{dT} = -\frac{a_2}{2} + \frac{1}{2} + \text{Re}\left(i\frac{\beta}{2}(a_1 e^{i(\varphi_1-\varphi_2)} - a_2)\right), \quad (S.I.8)$$

$$\frac{d\varphi_1}{dT} = \frac{\delta_1}{2} + \alpha a_1^2 + \text{Im}\left(i\frac{\beta}{2}\left(\frac{a_2}{a_1} e^{i(\varphi_2-\varphi_1)} - 1\right)\right), \quad (S.I.9)$$

and $$\frac{d\varphi_2}{dT} = \frac{\delta_2}{2} + \alpha a_2^2 + \text{Im}\left(i\frac{\beta}{2}\left(\frac{a_1}{a_2} e^{i(\varphi_1-\varphi_2)} - 1\right)\right). \quad (S.I.10)$$

To examine synchronized states we look at the oscillator phase difference $\phi=\phi_2-\phi_1$. Equations S.I.7-S.I.10 become $$\frac{da_1}{dT} = -\frac{a_1}{2} + \frac{1}{2} - \frac{\beta}{2}a_2\sin\varphi, \quad (S.I.11)$$

$$\frac{da_2}{dT} = -\frac{a_2}{2} + \frac{1}{2} + \frac{\beta}{2}a_1\sin\varphi, \quad (S.I.12)$$

and $$\frac{d\varphi}{dT} = \frac{d\varphi_2}{dT} - \frac{d\varphi_1}{dT} = \frac{\delta_2}{2} - \frac{\delta_1}{2} + \alpha a_2^2 - \alpha a_1^2 + \frac{\beta}{2}\left(\frac{a_1}{a_2} - \frac{a_2}{a_1}\right)\cos\varphi. \quad (S.I.13)$$

These are equations 1,2, and 3 from the main text where the prime character ' represents the derivative with respect to slow time T, and $$\frac{\delta_2}{2} - \frac{\delta_1}{2} = \Delta\omega.$$

II. Experimental Resonator Properties

In the experiment, devices were selected such that the parameters were nearly identical we show the experimental parameters of the two resonators. In Table S.1 we show the values for the resonator frequency and quality factor. For more information on how these are measured, please see reference 1. Note that throughout the course of the experiment (constant heating of the devices through the piezoresistive bias), the quality factors and frequencies may vary ~7%.

TABLE S.1

Table S.1. Fit parameters of the resonance plots shown below. The uncertainties in Q are found from measuring Q at different times throughout the experiment.

| Parameter | Device "1" | Device "2" |
|---|---|---|
| Frequency, $f_0$ | 13.056 MHz | 13.060 MHz |
| Q factor | 1640 ± 70 | 1680 ± 100 |

Figure 5:
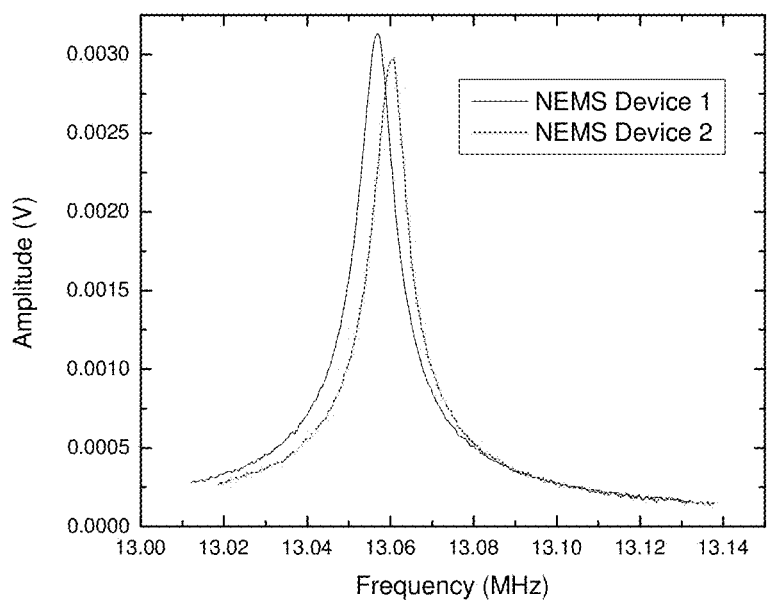

We also show the driven response from which the values of table S1 are found in FIG. 5. Note there are slightly different background conditions leading to the peak offset. The devices came from the same fabrication run and design.

III. Calibration of Setup, and Measurement of Synchronization Parameters

Figure 6:
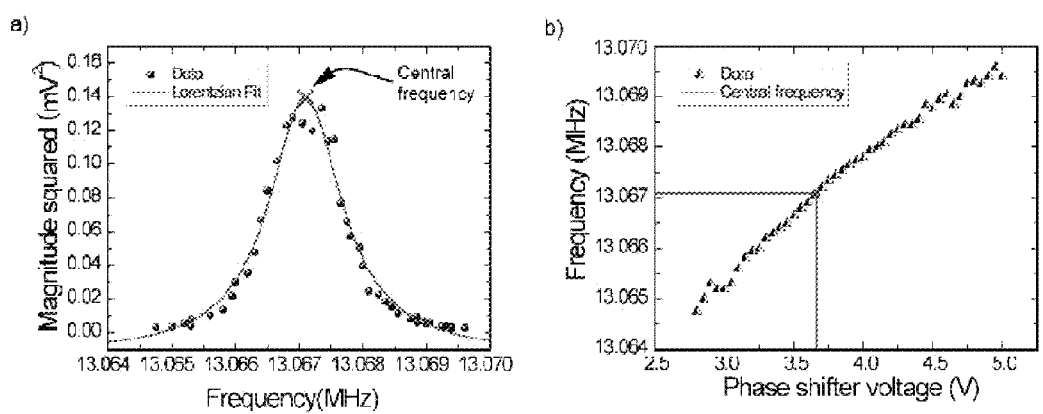

Before calibrating the three synchronization parameters (Δω, α, β), we must ensure that both the "oscillator" and "coupling" feedback signals (see FIG. 1 of the main text) have the proper phase shifts, i.e., $f_{1,2}$ is purely dissipative and $f_c$ is purely reactive in equations S.I.1 and S.I.2. If the oscillators are uncoupled, the proper phase shift in the "oscillator" feedback loops causes maximum oscillation. At low saturation, the oscillator magnitude is a Lorentzian[1] function with respect to the frequency. In the slow time, this is $$|\tilde{A}|^2 \propto \frac{s^2}{1+4\Omega^2}, \quad (S.II.1)$$

with $$\Omega = \frac{d\varphi_{1,2}}{dT}$$

from equations S.I.9 and S.I.10. We measure the oscillation amplitude and frequency as the phase shift in the oscillator loop is varied. We plot this for oscillator 1 in FIG. 6(a). A Lorentzian fit of this data yields the proper setting for the voltage controlled phase shifter embedded in the oscillator loop (the voltage controlled phase shifter is not pictured in FIG. 1 from the main text). From the Lorentzian fit, the central frequency gives us the proper setting for the phase shifter, as shown in FIG. 6(b).

A. Calibration of Coupling, β

In order to verify that the coupling loop is purely reactive, we compare two different measurements: 1) the level of amplification of the signal from the NEMS device through the coupling loop, and 2) the frequency shifts of the two oscillators due to the coupling feedback. Note that if the coupling is not strictly reactive, then according to reference 3, we must include a dissipative term to the feedback, $$f_c(A_1, A_2) = (K+i\beta)(A_2-A_1). \quad (S.II.2)$$

From FIG. 1 in the main text, if we turn off the second oscillator, then S.II.2 gives $$f_c(A_1, A_2) = (K + i\beta)(-A_1).$$  (S.II.3)

Figure 7:
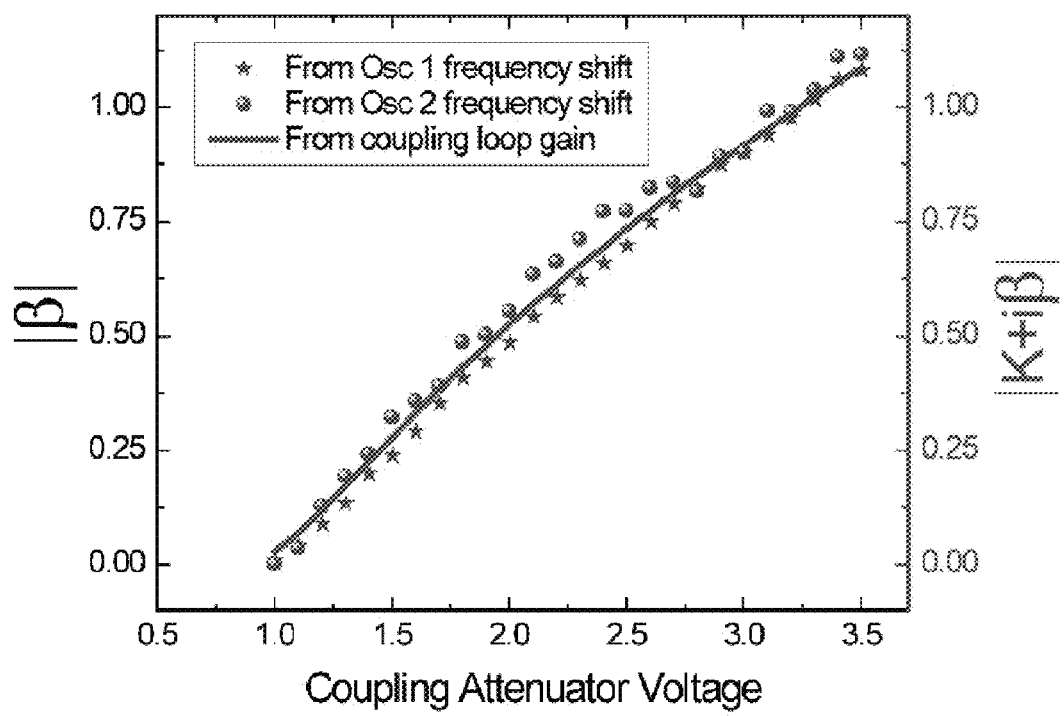

The feedback described in equation S.II.3, when inserted into equation S.I.5, will lead to not only tuning of the oscillator by $-\beta/2$, but also additional dissipation proportional to K. Note that the magnitude $|K+i\beta|$ is the total gain of a signal through the coupling loop. By measuring this coupling loop gain and comparing it to measurements of the oscillator frequency shift, we can verify that $|K+i\beta| = |\beta|$, i.e., our coupling is strictly reactive. In FIG. 7, $|K+i\beta|$ is measured by the first method (red line, right vertical axis), and $\beta$ is measured using the frequency shift of the two oscillators (blue stars and green circles, left vertical axis). If the red line had a larger magnitude than the data points from the frequency shifts, then there would be a dissipative component to the feedback ($K \neq 0$). However, these two measurements agree. These measurements not only verify that the coupling feedback has the proper phase shift, but also provide a calibration for coupling $\beta$ in terms of the voltage of the coupling attenuator.

B. Calibration of Frequency Pulling, $\alpha$

In order to calibrate the frequency pulling $\alpha = \lambda s^2$, we first calibrate the NEMS displacement and oscillator magnitude $|\tilde{A}|$. The thermomechanical noise of the NEMS device provides an absolute scale by which we can calibrate the device displacement from the electronic signal[2]. We can scale the NEMS displacement to the oscillator magnitude. With the oscillator and coupling feedback turned off, we measure the frequency response of the NEMS device under a constant level of external excitation. Fitting the NEMS frequency at the peak magnitude, for different values of excitation, yields the nonlinear coefficient $\lambda 1$. When the oscillators are uncoupled, the maximum oscillator amplitude corresponds to the level of saturation s (equation S.I.3 and S.I.4). Changes to the feedback saturation level, and thus the nonlinear pulling, can be made by adjusting the oscillator loop's attenuator after the limiting diode, as diagrammed in FIG. 1 of the main text.

C. Calibration of Detuning, $\Delta\omega$

We present two different ways of measuring the detuning $\Delta\omega$. When detuning is held fixed, a low value of coupling $\beta$ in equations S.I.11-S.I.13 yields a phase equation $$\frac{d\varphi}{dT} = \Delta\omega + \alpha a_2^2 - \alpha a_1^2 = \Delta\omega.$$  (S.II.4)

According to equation S.II.4, we can find the fixed detuning by measuring the oscillator frequency difference at zero coupling.

Figure 8:
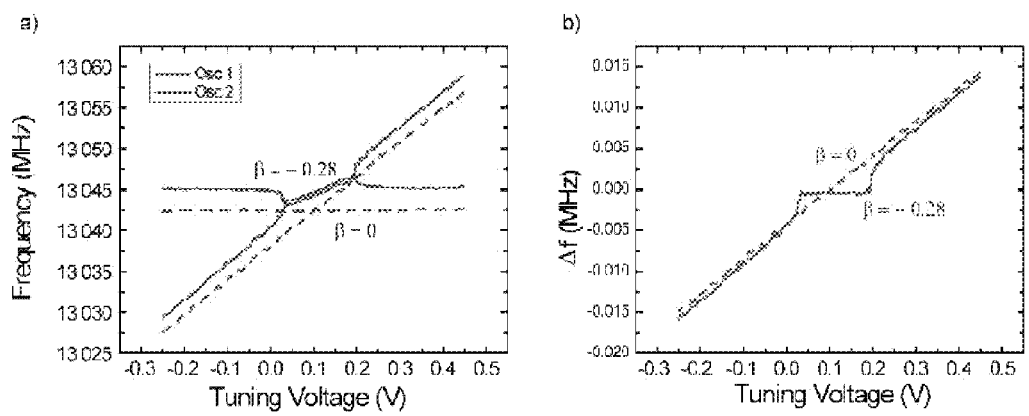

However, when the detuning is swept, a different calibration method is needed. In the experiment, we measure the oscillator frequency difference as a function of a piezoelectric tuning voltage (which changes the stress in one of the devices and hence the detuning[4]). We wish to make a correspondence between this tuning voltage and the detuning $\Delta\omega$. When the oscillators are far from the synchronization regime, the detuning dominates the other terms on the right hand side of equation S.I.13, so the oscillator frequency difference is proportional to the detuning. A linear fit to data far from the synchronized regime provides a relationship between the piezoelectric tuning voltage and the oscillator frequency difference. We therefore calibrate the detuning in terms of the piezoelectric tuning voltage by means of the oscillator frequency difference at data points far from synchronization. The calibration takes advantage of the fact that the detuning is linear in the piezoelectric tuning voltage[5]; we can interpolate each linear fit and calibrate the detuning in the synchronization regime. In FIG. 8(a), we show the raw data for the frequencies of the two oscillators from two sweeps with different coupling. In FIG. 8(b), for the same sweeps, we show the (unsealed) oscillator frequency differences, where the linear fits are performed.

The time between the measurements for the two different values of coupling hours, thus allowing drifts in oscillator frequencies to set in. However, the drift within each sweep is small, given that each sweep ~minutes. Therefore, through the method outlined above, each sweep can be calibrated to correct for these drifts.

Note that in FIG. 8(a), with the coupling turned on, there is mutual entrainment, evidence that our coupling is symmetric. Adler's equation (equation 4 from the main text) originally described[6] an experiment where oscillator 1 is fed the signal of oscillator 2, but oscillator 2 is not fed the signal of oscillator 1. This asymmetric coupling led to oscillator 1, the "slave" oscillator, being dominated by oscillator 2, the "master" oscillator. In our experiment, it is clear that both oscillator frequencies shift towards one another, i.e., each oscillator has equal influence over the final state.

IV. Notes on the Phase Noise Measurement

For the data for FIG. 4 the phase of the oscillator feedback was adjusted to make the noise of the two oscillators identical[1]. This changes equations 1-3 from the main text and so alpha and delta omega cannot be well-defined. However, the coupling (which is the same as in the primary experiment) is very small and mutually symmetric, and so the overall behavior follows two simple phase oscillators. From theory we cannot quantify when the synchronization will occur, but we find it more important to have identical noise so that we may demonstrate equivalent noise reduction, than to compare to the coherent dynamical model which was already confirmed in FIGS. 2,3. Noise experiments which detail synchronization when oscillator noise is not identical is not described herein.

REFERENCES FOR SUPPLEMENTAL INFORMATION

1 Villanueva, L. G. et al. Surpassing fundamental limits of oscillators using nonlinear resonators. arXiv:1210.8075 (2012).
2 Villanueva, L. G. et al. A Nanoscale Parametric Feedback Oscillator. *Nano Letters* 11, 5054-5059, doi:10.1021/n12031162 (2011).
3 Cross, M. C., Rogers, J. L., Lifshitz, R. & Zumdieck, A. Synchronization by reactive coupling and nonlinear frequency pulling. *Physical Review E* 73, 036205 (2006).
4 Karabalin, R. B. et al. Signal Amplification by Sensitive Control of Bifurcation Topology. *Physical Review Letters* 106, 094102 (2011).
5 Karabalin, R. *Nonlinear, coupled, and parametric nanoelectromechanical systems*, California Institute of Technology, (2008).
6 Adler, R. A Study of Locking Phenomena in Oscillators. *Proceedings of the IRE* 34, 351-357 (1946).

Part Two: Provisional Application and Other Embodiments

Additional embodiments were particularly described in priority provisional application 61/719,205 filed Oct. 26, 2012 ("Synchronization of Nanomechanical Oscillators"), which is hereby incorporated by reference in its entirety for all purposes, including the Figures. Coupled oscillators can be used in networks.

Introduction

Synchronization is the locking of phase between distinct oscillators. Coupled oscillators, through the combination of interaction and nonlinearity, may lock together to oscillate coherently at a single frequency even if their intrinsic frequencies are different (e.g., due to slight fabrication differences). It has a variety of possible applications such as, for example, frequency sources, sensors, amplification, and neural networks. Here we describe synchronization between nanomechanical oscillators employing electronic feedback and electronic coupling. Electronic coupling can provide far easier coupling compared to mechanical or electrostatic coupling as these other methods can require that individual devices and elements be fabricated in very close proximity. Electrostatic coupling is noted in Agrawal et al., *Phys. Rev. Lett.*, 111, 084101 Aug. 23, 2013, and no admission is made that this reference is prior art. Also, light coupling is described in Zhang et al., *Phys. Rev. Lett.*, 109, 233906 (Dec. 7, 2012), but again no admission is made that this reference is prior art. Networks of oscillators and coupled oscillators can be formed including one-dimensional, two-dimensional, and three-dimensional networks.

A series of master circuit boards can be created that permit a wide range of nonlinear oscillator network topologies. The individual NEMS oscillator elements can be configured as small circuit boards that are themselves "pluggable" into these master topology boards.

First a single oscillator and its topology will be understood, after which multiple oscillator diagrams and circuits will be presented.

A single Nanomechanical Feedback Oscillator

Figure 9:
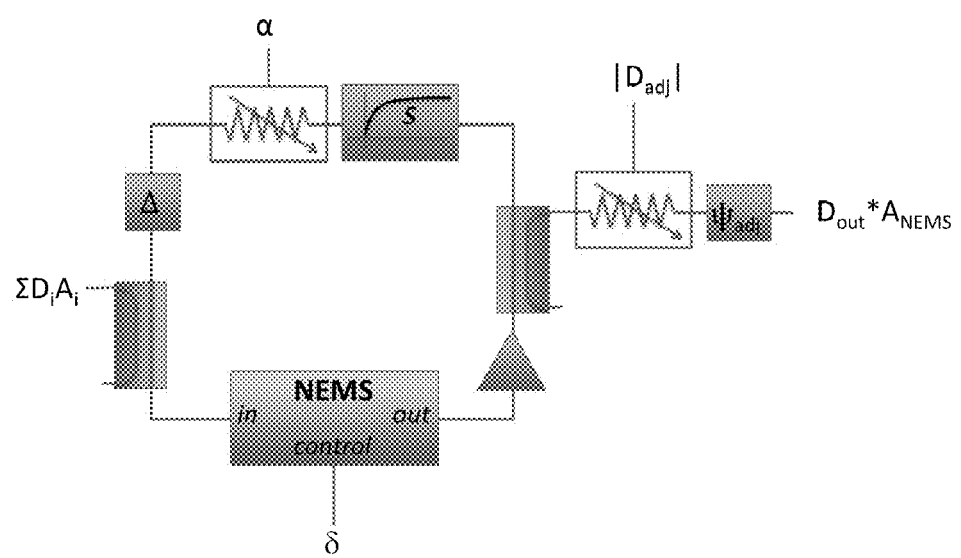

A single nanomechanical oscillator diagram is shown in FIG. 9. It includes a nanoelectromechanical resonator (NEMS) which has an input port (where the device is actuated), an output port (where the device is detected), and a port to control the device resonant frequency, labeled δ. Here δ specifies the frequency of the device in the rotating frame. The frequency control can be accomplished by modifying stress (through piezoelectric or thermal means), or through a capacitive gate.

Each NEMS input and output port has a directional coupler attached in order to feed the oscillator signal to other devices. Here they are labeled $D_i$, $D_{out}$. These two signals constitute the coupling in and coupling out, respectively. The input coupling is a combination of external signals, typically from other NEMS devices. Here the coupling terms are a combination of real and imaginary parts. As shown, the output coupling magnitude can be controlled through use of attenuation, whose control parameter is labeled $|D_{adj}|$. Its phase is adjusted through $\psi_{adj}$. Each coupling signal can be written $D=|D|e^{i\psi}=K+i\beta$ where K is the dissipative coupling and β is the reactive coupling.

The NEMS device typically has frequency-amplitude nonlinearity (a Duffing term). The frequency-nonlinearity in combination with the amplitude control elements (the saturation s and the controllable attenuator) constitute the frequency pulling, α. The saturation removes the dependence of the feedback signal on the output of the device displacement, while the attenuator combination sets the magnitude of the feedback (this also can be controlled by auto-gain control amplifiers). The phase of the feedback can be controlled with a phase shifter ϕ (typically set to π/2) to achieve the Barkhausen criterion for the individual oscillators.

The equation for such a system can be written $$\frac{d\tilde{A}_{NEMS}}{dT} + \frac{\tilde{A}_{NEMS}}{2} - i(\delta + \alpha|\tilde{A}_{NEMS}|^2)\tilde{A}_{NEMS} = \qquad (1)$$
$$-\frac{is}{2}e^{i(\phi_{NEMS}+\Delta)} + \frac{1}{2}\sum_I D_I \tilde{A}_i;$$

$$\tilde{A}_{NEMS} = \tilde{a}_{NEMS}e^{i\phi_{NEMS}}$$

where $\phi_{NEMS}$ is the phase of the NEMS device in a frame rotating with the resonant frequency of the device. Thus, external signals will always have a subscript and we drop it for the NEMS device ($\tilde{A}_{NEMS}=\tilde{A}$). We can scale this equation by s ($\tilde{A}=A*s$) and divide by s to get, $$\frac{dA}{dT} + \frac{A}{2} - i(\delta + \tilde{\alpha}s^2|A|^2)A = -\frac{i}{2}e^{i(\phi+\Delta)} + \frac{1}{2}\sum_i (K_i + i\beta_i)A_i; \qquad (2)$$

We can rewrite this equation in terms of real and imaginary parts and choose a scaled frequency pulling $\tilde{\alpha}s^2=\alpha$ $$\frac{da}{dT} = -\frac{a}{2} + \frac{\sin\Delta}{2} + \frac{1}{2}\text{Re}\left[\sum_i (K_i + i\beta_i)A_i * e^{-i\phi}\right] \qquad (3)$$

$$\frac{d\phi}{dT} = \delta + \alpha a^2 - \frac{\cos\Delta}{2} + \frac{1}{2}\text{Im}\left[\sum_i (K_i + i\beta_i)\frac{A_i}{A}\right] \qquad (4)$$

Thus in the scaled equations, control of saturation (or level of oscillation) sets the level of frequency pulling.

If the input signals are harmonic $A_i=a_i e^{i\phi_i}$, then we get $$\frac{da}{dT} = -\frac{a}{2} + \frac{\sin\Delta}{2} + \frac{1}{2}\sum_i K_i a_i \cos(\phi_i - \phi) + \frac{1}{2}\sum_i \beta_i a_i \sin(\phi_i - \phi) \qquad (5)$$

$$\frac{d\phi}{dT} = \delta + \alpha a^2 - \frac{\cos\Delta}{2a} - \frac{1}{2}\sum_i K_i \frac{a_i}{a}\sin(\phi_i - \phi) + \frac{1}{2}\sum_i \beta_i \frac{a_i}{a}\cos(\phi_i - \phi) \qquad (6)$$

The phase approximation can be taken when $a_i \approx 1$. For $$\frac{da}{dT} = 0$$

(a fixed point m amplitude)

$$\frac{d\phi}{dT} = \delta + \alpha - \frac{\cos\Delta}{2} + \frac{1}{2}\sum_i K_i \sin(\phi_i - \phi) + \frac{1}{2}\sum_i \beta_i \cos(\phi_i - \phi) \qquad (7)$$

In the absence of frequency pulling and at Δ=π/2 and we get:

$$\frac{d\phi}{dT} = \phi + \frac{1}{2}\sum_i K_i \sin(\phi_i - \phi) \qquad (8)$$

which is the Kuramoto model.

Two Oscillator Topologies

Figure 10:
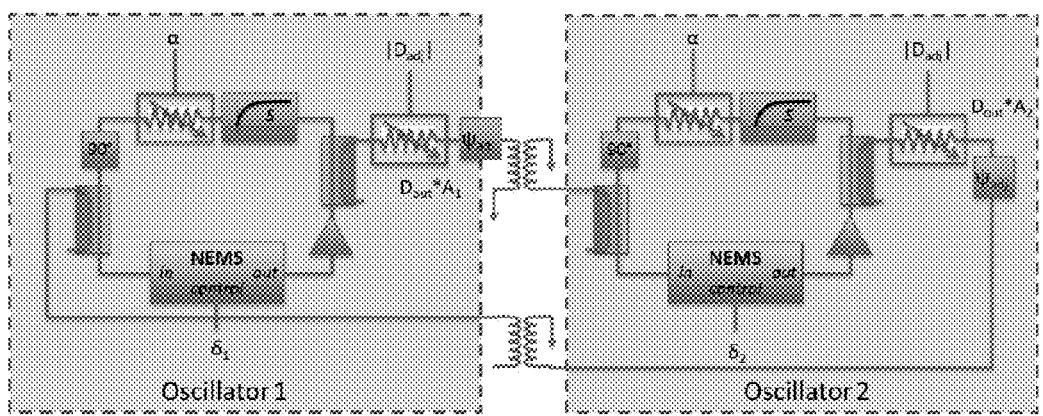

Here we present some basic two oscillator topologies and discuss their couplings. First we discuss "Direct Coupling" as shown in FIG. 10.

Figure 11:
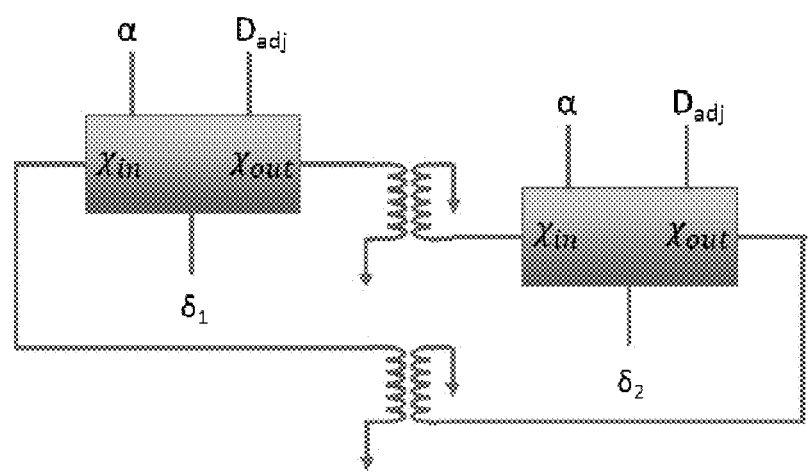

We can equate this to FIG. 11, where $D_{out}A_{NEMS}=X_{out}$ for each oscillator and $D_{adj}$ adjusts both phase and magnitude of the output coupling. The equation for such a system (with phase $\Delta$ of each oscillator set to $$\frac{\pi}{2})$$

is given by $$\frac{da_1}{dT} = -\frac{a_1}{2} + \frac{1}{2} + \frac{1}{2}K_2 a_2 \cos(\phi_2 - \phi_1) - \frac{1}{2}\beta_2 a_2 \sin(\phi_2 - \phi_1) \quad (9)$$

$$\frac{da_2}{dT} = -\frac{a_2}{2} + \frac{1}{2} + \frac{1}{2}K_1 a_1 \cos(\phi_1 - \phi_2) - \frac{1}{2}\beta_1 a_1 \sin(\phi_1 - \phi_2) \quad (10)$$

$$\frac{d\phi_1}{dT} = \delta_1 + \alpha a_1^2 + \frac{1}{2}K_2 \frac{a_2}{a_1}\sin(\phi_2 - \phi_1) - \frac{1}{2}\beta_2 \frac{a_2}{a_1}\cos(\phi_2 - \phi_1) \quad (11)$$

$$\frac{d\phi_2}{dT} = \delta_2 + \alpha a_2^2 + \frac{1}{2}K_1 \frac{a_1}{a_2}\sin(\phi_1 - \phi_2) - \frac{1}{2}\beta_1 \frac{a_1}{a_2}\cos(\phi_1 - \phi_2) \quad (12)$$

For synchronization we wish examine phase locked states, i.e.

$$\frac{d\phi_2}{dT} - \frac{d\phi_1}{dT} = \frac{d}{dT}(\phi_2 - \phi_1) = \frac{d\phi_d}{dT} = 0,$$

which gives $$\frac{da_1}{dT} = -\frac{a_1}{2} + \frac{1}{2} + \frac{1}{2}K_2 a_2 \cos\phi_d - \frac{1}{2}\beta_2 a_2 \sin\phi_d \quad (13)$$

$$\frac{da_2}{dT} = -\frac{a_2}{2} + \frac{1}{2} + \frac{1}{2}K_1 a_1 \cos\phi_d + \frac{1}{2}\beta_1 a_1 \sin\phi_d \quad (14)$$

$$\frac{d\phi_d}{dT} = (\delta_2 - \delta_1) + \alpha(a_2^2 - a_1^2) + \quad (15)$$

$$\frac{1}{2}\left[K_2 \frac{a_2}{a_1}\sin\phi_d + K_1 \frac{a_1}{a_2}\sin\phi_d + \beta_1 \frac{a_1}{a_2}\cos\phi_d - \beta_2 \frac{a_2}{a_1}\cos\phi_d\right]$$

which for symmetric coupling ($K_1=K_2=K$, $\beta_1=\beta_2=\beta$) gives, $$\frac{d\phi_d}{dT} = \quad (16)$$

$$(\delta_2 - \delta_1) + \alpha(a_2^2 - a_1^2) + \frac{1}{2}\left[\left(\frac{a_2}{a_1} + \frac{a_1}{a_2}\right)K\sin\phi_d - \left(\frac{a_2}{a_1} - \frac{a_1}{a_2}\right)\beta\cos\phi_d\right]$$

which reduces to the Adler equation for $K=0$, $\beta<0.1<<\alpha$ $$\frac{d\phi_d}{dT} = (\delta_2 - \delta_1) + 4\alpha\beta\sin\phi_d \quad (17)$$

Figure 12:
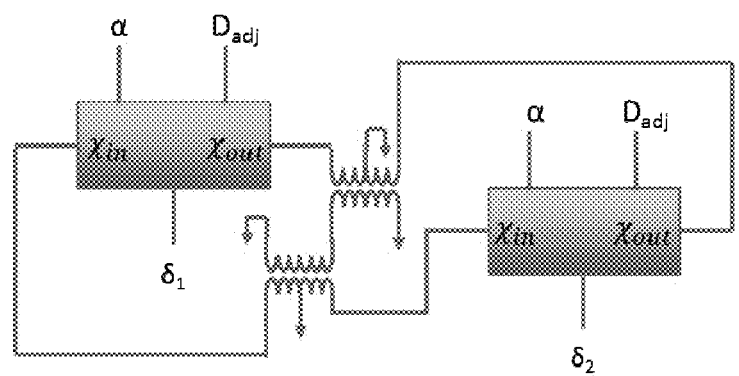

Another oscillator topology can be made where the coupling in is the difference of the oscillators ($X_{in,1}=X_{out,2}-X_{out,1}$, $X_{in,2}=X_{out,1}-X_{out,2}$), which looks like the topology of FIG. 12.

Types of Coupling

The previous description centered on nearest-neighbor coupling. However, when electronic coupling is employed various regular array topologies can be realized. We described a range of coupling, including all-to-all, power-law, and nearest-neighbor.

Mean-Field Coupling

Figure 13:
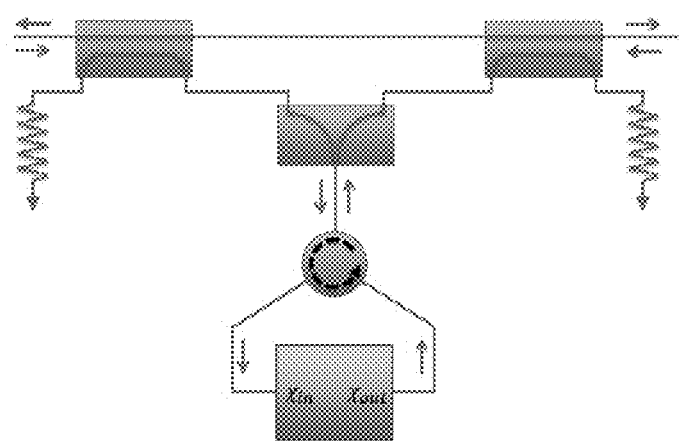
Figure 14:
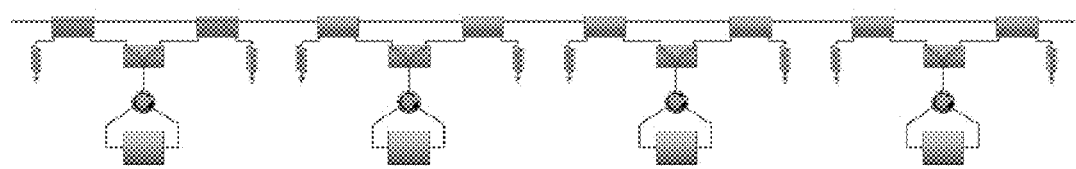

All-to-all coupling is the case where every oscillator is equally coupled to all the other oscillators. This can be accomplished through a variety of circuits. FIG. 13 shows a circuit where they are coupled (through a directional coupler) to a common transmission line. A microstrip transmission line can be used in conjunction with printed circuit boards. Note that a circulator can be replaced with two isolators (either passive or active) with two different signal lines, which, when multiple oscillators are attached looks like FIG. 14. More oscillators can exist on the transmission line.

Long Range Coupling

Figure 15:
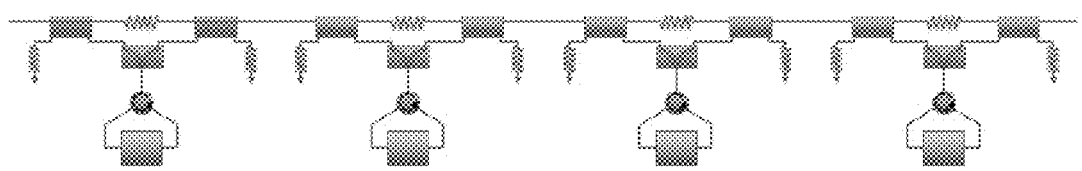

For regular oscillator chains we can generalize the coupling to spread over several oscillators (but not all). Such a topology is shown in FIG. 15.

Here similar attenuators are inserted between nodes in order to create larger coupling attenuation along the oscillator chain. For zero attenuation (shorting the circuit at the attenuator) we get a mean-field lattice, and for infinite attenuation (opening the circuit at the attenuator) we get a nearest-neighbor chain. Assuming an attenuation in power $\lambda^2$ per attenuator we get a coupling of the form $$\chi_{in,r \to i} = 2 * \chi_{out,i+r} = 2 * \frac{\chi_{out,r}}{\lambda^{r-i-1}}.$$

Figure 16:
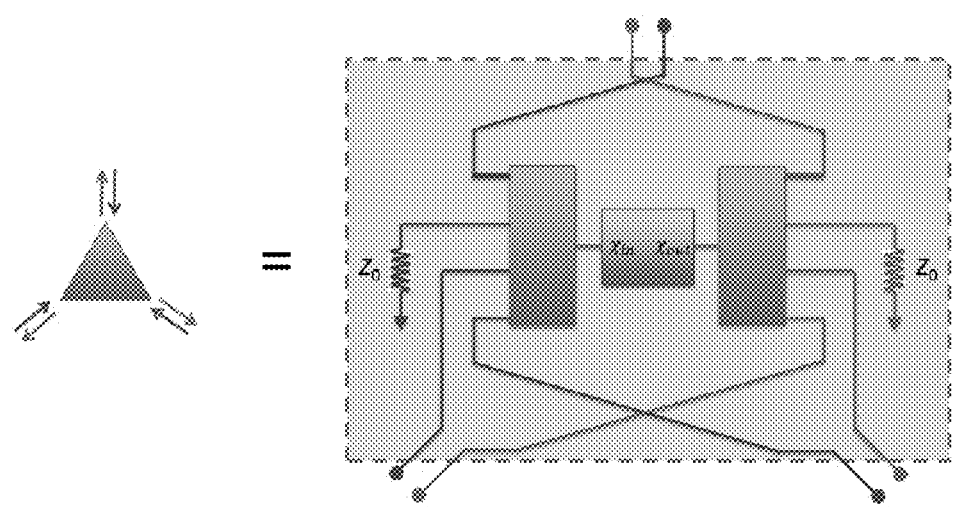

This exponential decay can be controlled by adjusting the level of attenuation. We do not show the case of nearest neighbor coupling with the transmission line since it is accomplished by using the circuit in FIG. 16 and increasing the attenuation.

Chimera states can be created and studied. A recently discovered phenomena in arrays of identical oscillators, is that the population may spontaneously split into two groups, one synchronized and one unsynchronized, so that coherent (synchronized) dynamics and incoherent (unsynchronized) dynamics coexist. The existence of these states relies on couplings longer range than nearest neighbor. The prediction of these states is based on theories for the $N \to \infty$ limit. More recent work has suggested that the states are actually transients in finite systems, but with a lifetime scaling exponentially with the system size N, which becomes hard to investigate numerically as N increases. The present NEMS arrays, in which longer-range couplings are easily engineered and time scales are short, can be used to study these remarkable states

Nearest-Neighbor Networks Off the Transmission Line

Nearest-neighbor networks, both regular and random, can be manufactured through the use of single connections between oscillators. Note that throughout all these circuits we keep control over $\delta$, $\alpha$, $D_{adj}$. We can create a regular triangular lattice with the single element (which we call the oscillator unit cell) shown in FIG. 16.

Figure 17:
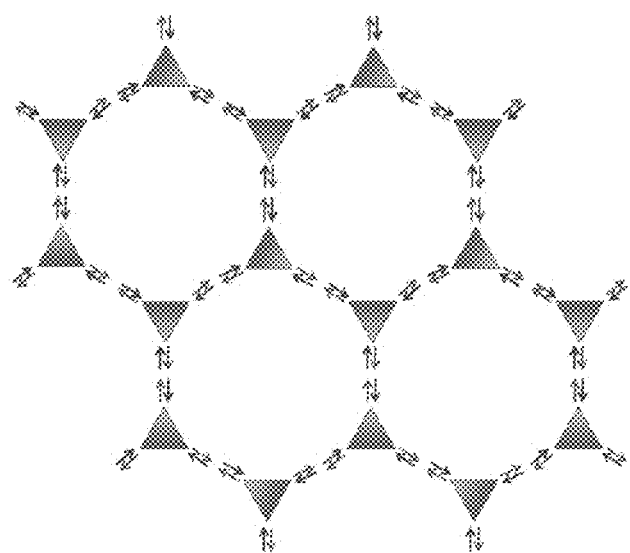

Here the oscillator coupling input and output are connected to power splitter/combiners so that three signals can go into and out of the oscillator. We can arrange a lattice as below in FIG. 17.

Figure 18:
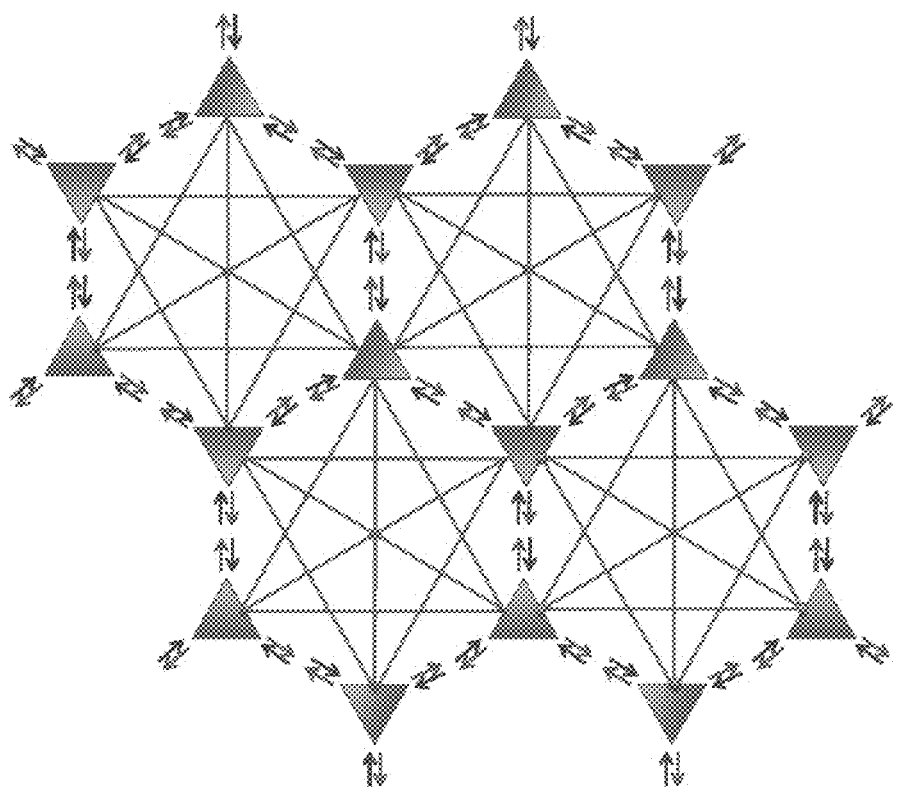

This gives a regular 2-dimensional hexagonal lattice of oscillators. We can create more tightly connected lattices (a network of larger average degree) by including connections within hexagons. FIG. 18 shows such a lattice where the orange and green connections do not overlap (and are bidirectional; they represent both blue and red lines). We must include more power combiners/splitters for this operation.

Figure 19:
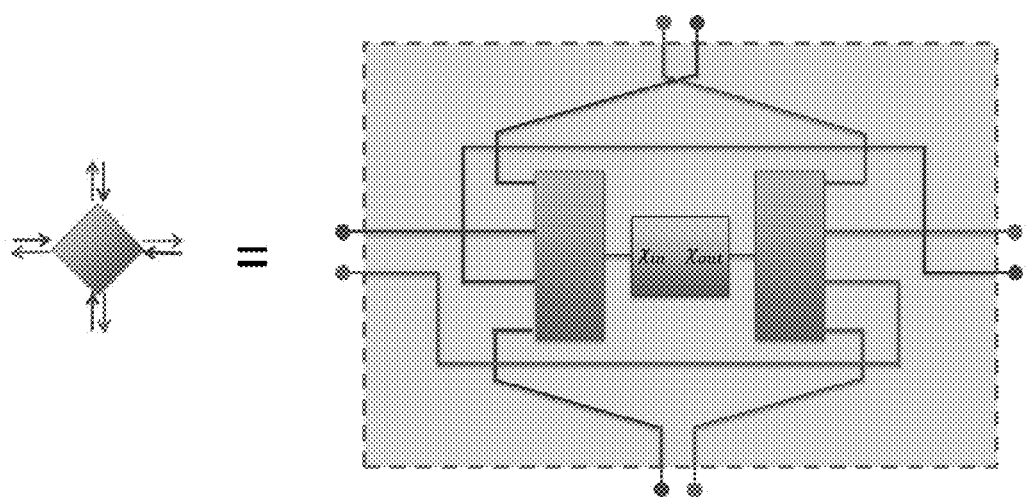

With either (or both) of these connections (orange, green) the network synchronization regime grows for a fixed amount of coupling. A square lattice can be constructed using the element in FIG. 19.

Figure 20:
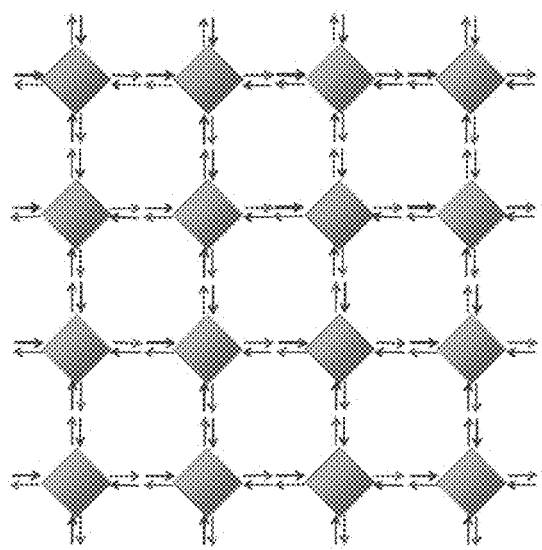

We can construct a lattice out of this oscillator unit cell (with four connections per oscillator). This is shown in FIG. 20.

Figure 21:
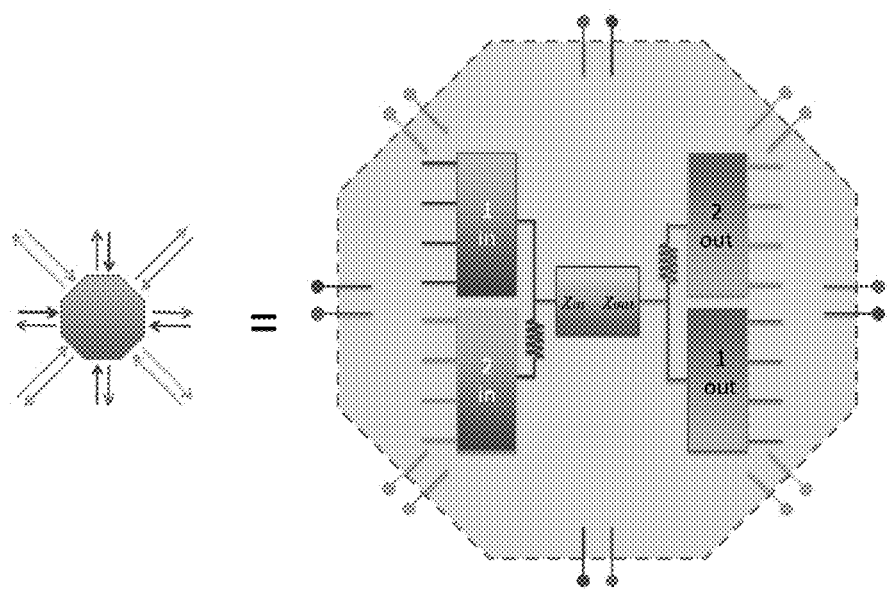

We can make a lattice with two magnitudes of overlapping lattice coupling. We construct the oscillator unit cell as in FIG. 21.

Figure 22:
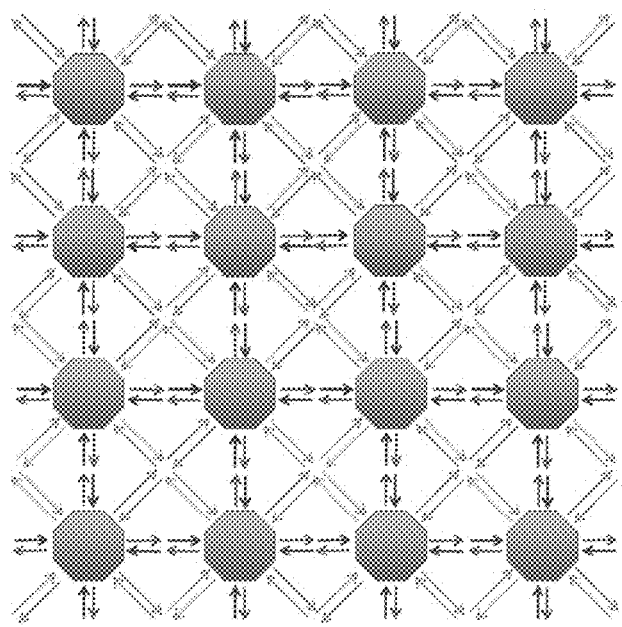

In this oscillator unit cell the attenuators can be adjusted. We show a lattice of the kind in FIG. 22.

Figure 23:
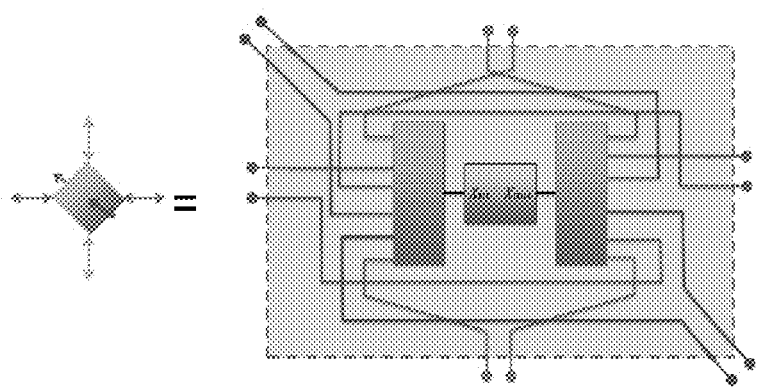

We can also envision making regular arrays in higher dimensions. We can make a unit cell for a 3-d cubic lattice, such as in FIG. 23.

Figure 24:
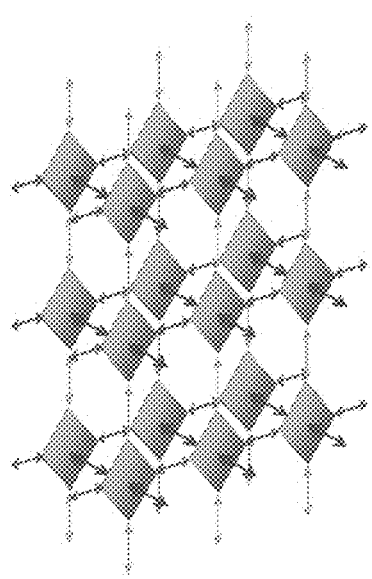
Figure 25:
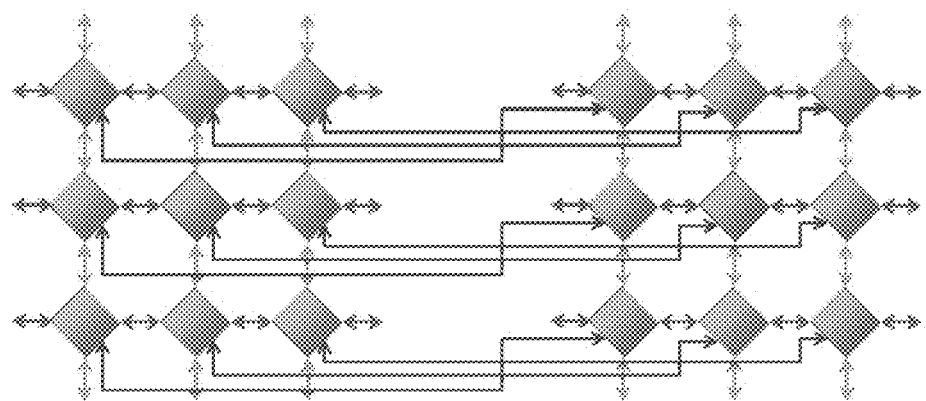

The topology for the lattice is envisioned in FIG. 24.

To make this in planar structures by using circuits we can connect the 2-d square arrays side-by-side electronically.

Novel Behavior in Two-Dimensional Lattices

2-D lattices, some of which are described above, are a natural practical architecture for easily fabricated oscillator arrays and provide access to novel physical phenomena. For example, topological synchronized states are intrinsic to the system, and do not rely on the topology induced by boundary conditions. In two dimensions, vortex-like topological states—in which the phase winds around a point in the plane—are intrinsic. Such topological defects play a vital role in phase transitions in two dimensional equilibrium systems. These vortices are believed to be important in the breakdown of the synchronized state. With reactive coupling, these vortices form spiral sources of waves, as seen in the result of a simulation (not shown). Such spirals are also seen in other physical, chemical and biological systems. One important practical example is the spiral waves in heart muscle tissue though thought to be the cause of certain arrhythmias in the heart.

There are other examples of system dynamics that differ as the dimension (or more generally topology) of the network changes. In a one-dimensional chain, synchronization with t phase difference between adjacent oscillators (for example due to repulsive phase interaction) can be trivially mapped onto the attractive problem. This is not possible in two or higher dimensions, so that the alternating-a synchronized state, analogous to the antiferromagnetic state of spins in the solid state, becomes a distinct synchronized state with novel properties. For example, injection locking of the synchronized state to an external periodic signal, the phases will lock at approximately $\pi/2$ to the drive phase, since it is not possible to lock both sublattices at zero phase (again this is analogous to an antiferromagnet in an external field). This state has been suggested to have interesting noise reduction properties.

Random Networks

Figure 26:
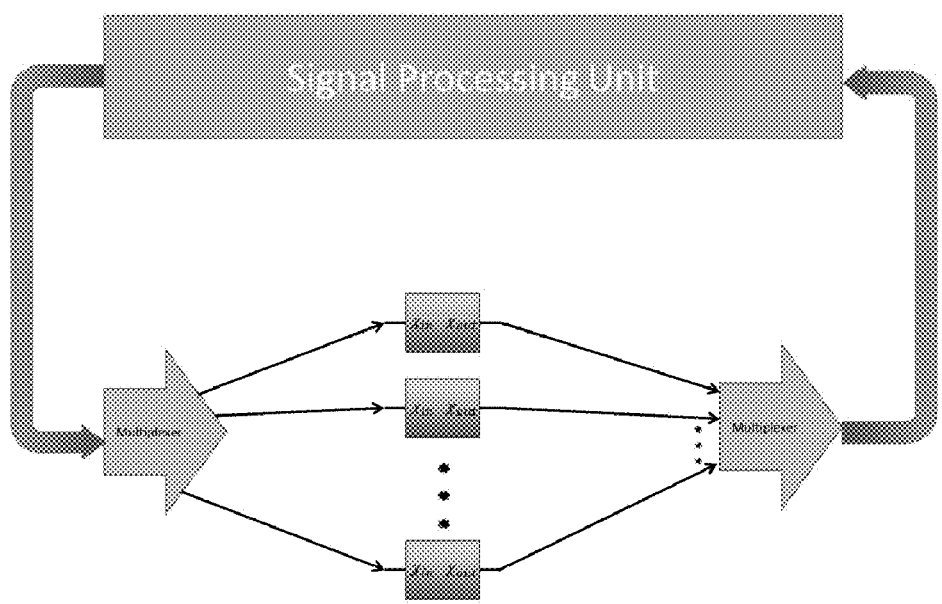

Random networks can be created (and adjusted) in real time through the use of electronic signal processing. In FIG. 26, we show a general topology for a network whose connections are determined by a central electronic signal processing unit. Through this electronic signal processing unit, all the networks previously described can be made in addition to random networks with connections determined statistically.

Applications of Synchronized Networks

Frequency sources can be made out of the synchronized oscillators. Also sensor networks can be made which respond to global stimuli (in order to improve sensitivity of the global stimulus) or used to transmit information.

When a global stimulus (such as gas, acceleration, temperature, pressure, etc.) is input into a synchronized array of N oscillators, the average frequency of the array changes as much as if one oscillator were stimulated, but with N times less phase noise power. Given the same signal with less noise a better signal-to-noise ratio makes a more sensitive detector. When disorder is set into the array, waves can propagate from "source" oscillators. We can modulate the "source" frequency to send information across the oscillator array.

Other applications for oscillators known in the art can be carried out.

Ring Embodiment

Figure 27:
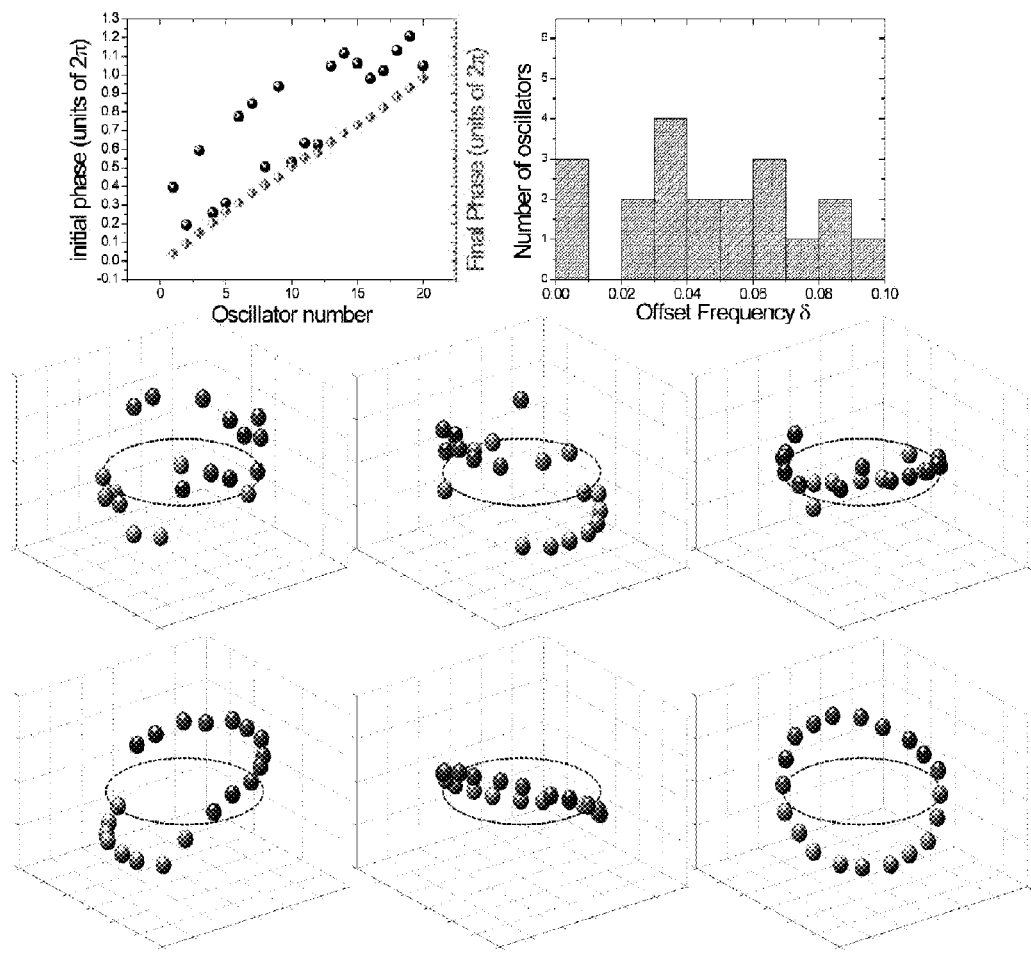

For chains of oscillators connected as a ring (linear chains can be made into a ring by connecting the ends together), synchronized states of disconnected topologies may be found, namely with different integral winding numbers of the phase around the ring. In addition to the quasi-uniform state, in which the oscillators synchronize to roughly equal phases (with small phase differences to counteract the small frequency differences), splay states in which adjacent phases are rotated by about $2\pi n/N$, with n the integral winding number, may also be exist. If there are reactive components to the coupling, these states will consist of waves of phase propagating around the ring. In FIG. 27, we show a simulation of a coupled oscillator ring with a total initial phase winding number of 1, which gives a wave propagating around the ring and smoothes out phase imperfections (FIG. 27*a*) even in the presence of dispersion (FIG. 27*b*). The topology of the ring remains constant while the propagating wave (FIG. 27*c*) shows this evolution in time (left to right, top to bottom). These splay states provide a way of building a tunable (in discrete steps) high precision frequency source. The noise averaging in the splay states, potentially yielding improvement in frequency precision, has not yet been studied.

Oscillator Mini-Board Diagram

Figure 28:
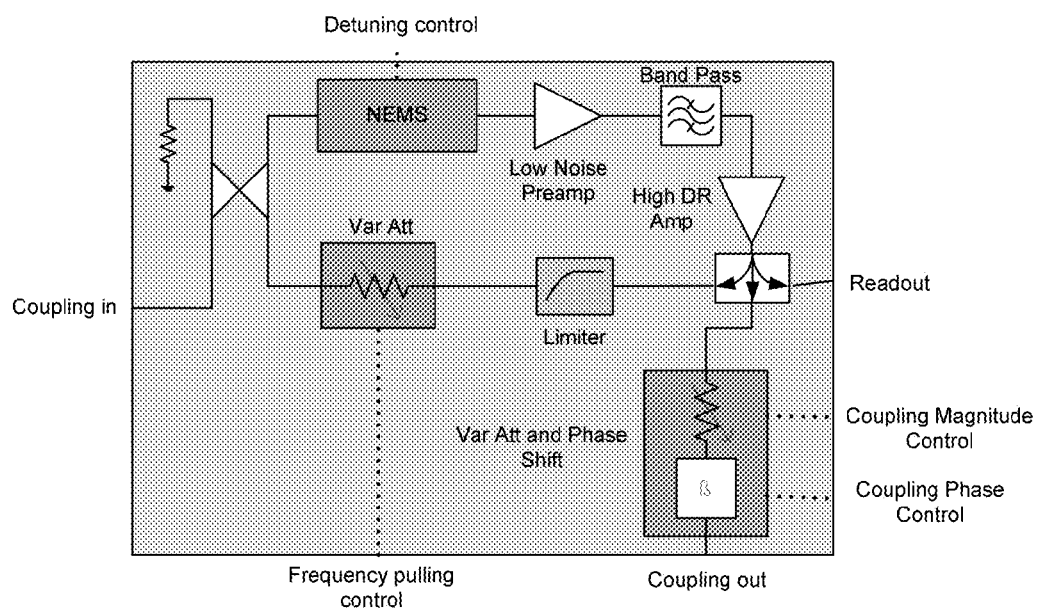

Each oscillator can be constructed using its own circuit board; these boards can be mounted on a larger "bus and control" board. FIG. 28 shows a "mini-board" embodiment which holds a NEMS oscillator. In one embodiment, this board is no larger than 25 cm$^2$, given the components shown on this board. This gives total "bus and control" board size (for front and back mounting of 96 "mini-board" oscillators) of at least 1,200 cm$^2$ plus additional components for buses and control. Since each oscillator is pluggable, one can measure and calibrate their parameters individually, and then plug them into a large "bus and control" board.

Coupling Bus

Two designs are provided for a coupling bus.

The first design uses a common bus with an attenuator embedded (FIG. 15) in the bus. We can make these attenuators variable and continuously modify them through a control voltage. This gives us access to "all-to-all" coupling, "exponential decay" coupling, and "nearest-neighbor" on a 1-d bus. We call this the "1-D bus".

The second design relies on sending each coupling signal to a crosspoint switch matrix where we could create higher dimensional or complex networks. A 96×96 crosspoint switch matrix can be made from smaller crosspoint switch matrices available from CMOS manufacturers (for example 9 AD 8118 32×32 switches). The multilayer board is important to routing these different coupling signals to the smaller crosspoint switches. This crosspoint switch matrix gives programmable network topologies, mitigating any costs of creating new boards. We call this the "crosspoint switch bus".

Readout Bus and Data Processing

The most important part of the readout bus is to identify each oscillator in the array, while not interfering with the coupling between oscillators.

One needs to readout only at 1 MHz even though our oscillators frequency is 100 MHz. This is because the oscillators' dynamics respond at a rate close to the decay time, as set by the dissipation of the mechanical device. The NEMS devices we use have quality factors between 100-3000, setting relevant bandwidths below 1 MHz. Although, low Q improves data acquisition rates, high Q gives better oscillator performance, which is useful for frequency generation and sensing. Therefore, if we mix the oscillator signals from 100 MHz down to any frequency above 1 MHz, we still capture the relevant dynamics.

Figure 29:
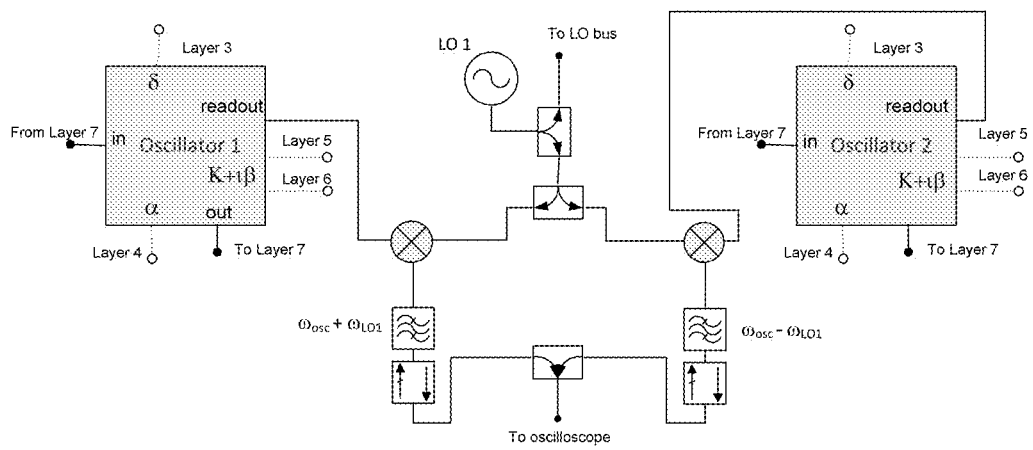

In order to correctly identify each oscillator, one can multiplex into a range of frequency bands, with each oscillator its own frequency band. One can read out the signals coming from the board in a 4-channel oscilloscope, where 3 of the channels have frequency multiplexed signals (each channel 32 NEMS oscillators in 32 frequency bands), and the 4th channel reserved for the local oscillator frequencies used to mix the NEMS oscillator signals. As shown in FIG. 29, a local oscillator can be used to upconvert and downconvert two separate oscillators into different frequency bands. One therefore needs 16 oscillators on board, giving 32 frequency bands on 3 input channels. Thus we will have 96 oscillators identified. By using isolators, we can ensure that the readout will not interfere with the coupling bus.

With 1 Gpt memory, one can take 10 second data (or more, depending on frequency multiplexing), or see behavior (at slow time dynamics) of $10^6$ 'cycles'. With this real-time continuous data, one can truly see the glassy behavior of these systems.

After the data has been collected, digital filtering of the local oscillator channel with the NEMS channels can pick out the individual NEMS signals. After which, we can use numerical correlation to find synchronization behavior between separate oscillators.

What is claimed is:

1. A device to provide synchronized distinct oscillators comprising:
   a plurality of distinct oscillators including a first distinct oscillator and a second distinct oscillator,
   the first distinct oscillator comprising a first nanoelectromechanical resonator adapted to function as part of the first distinct oscillator, an input port, an output port, and a port to control device resonance frequency;
   the second distinct oscillator comprising a second nanoelectromechanical resonator adapted to function as part of the second distinct oscillator, an input port, and output port, and a port to control device resonance frequency;
   electronic circuitry electronically coupled to the distinct oscillators and adapted so that the distinct oscillators are synchronized with use of electronic feedback, wherein each distinct oscillator produces a signal, and the signal from each distinct oscillator is split into two different feedback loops, wherein one of the two different feedback loops is an oscillator loop for creating self-sustained oscillations, and the other is a coupling loop to synchronize distinct oscillators.

2. The device of claim 1, wherein, for each oscillator, the coupling loop of the oscillator is coupled to the coupling loop of at least one other oscillator.

3. The device of claim 1, wherein the coupling loop of at least one oscillator is inductively coupled to the coupling loop of at least one other oscillator.

4. The device of claim 1, wherein the oscillator loop is dissipative, and the coupling loop is reactive.

5. The device of claim 1, wherein the oscillator loop is dissipative, and the coupling loop is reactive, wherein, for each oscillator, the oscillator loop is adapted to produce a nonlinear feedback signal in response to an oscillation amplitude signal; and the coupling loop is configured to produce signal that depends substantially linearly on a frequency detuning of the oscillator from at least one other coupled oscillator.

6. The device of claim 1, wherein in the oscillator loop a signal is amplified with gain g and then sent through a saturating limiter.

7. The device of claim 1, wherein in the oscillator loop a signal is amplified with gain g and then sent through a saturating limiter and then to a voltage controlled attenuator after each limiter which sets a level of oscillation.

8. The device of claim 1, wherein the coupling loop comprises a common loop common to the two oscillators, wherein a signal is amplified so that a voltage controlled attenuator adjusts the signal level in the common loop, thereby setting the coupling strength.

9. The device of claim 1, wherein a frequency difference is controlled by adjusting the stress induced in one of the resonators by a piezovoltage.

10. The device of claim 1, wherein the device provides for three parameter controls ($\Delta\omega,\alpha,\beta$) which are independent, wherein $\Delta\omega$ is the difference between resonant frequencies of the resonators, $\alpha$ is the amount of frequency pulling, and $\beta$ is the coupling strength.

11. The device of claim 1, wherein the device provides for three parameter controls ($\Delta\omega,\alpha,\beta$) which are controlled by independent and external DC voltage sources, wherein $\Delta\omega$ is the difference between resonant frequencies of the resonators, $\alpha$ is the amount of frequency pulling, and $\beta$ is the coupling strength.

12. The device of claim 1, wherein the oscillators are coupled in a one-dimensional chain.

13. The device of claim 1, wherein the oscillators are part of a multidimensional network.

14. The device of claim 1, wherein the oscillators are part of a two-dimensional network.

15. The device of claim 1, wherein the oscillators are part of a three-dimensional network.

16. The device of claim 1, wherein the oscillators are part of a random network.

17. The device of claim 1, wherein each oscillator is equally coupled to all other oscillators.

18. The device of claim 1, wherein the oscillators are coupled through a transmission line.

19. The device of claim 1, further comprising a coupling bus adapted to provide selectable coupling of the oscillators.

20. The device of claim 1, further comprising a coupling bus adapted to provide selectable coupling of the oscillators, wherein the selectable coupling is at least one of all-to-all coupling, nearest-neighbor coupling, or decaying coupling.

21. The device of claim 1, wherein some but not all of the oscillators are coupled.

22. The device of claim 1, wherein at least one attenuator is used between oscillators.

23. The device of claim 1, wherein the oscillators form part of an oscillator lattice.

24. The device of claim 1, wherein the oscillators form part of a triangular lattice.

25. The device of claim 1, wherein the oscillators form part of a hexagonal lattice.

26. The device of claim 1, wherein the oscillators form part of a square lattice.

27. The device of claim 1, wherein the device comprises two to 99 oscillators.

28. The device of claim 1, wherein the device comprises at least 100 oscillators.

29. The device of claim 1, wherein the device comprises at least 10,000 oscillators.

30. The device of claim 1, wherein the control of device resonance frequency is adapted to be carried out by modifying stress, by piezoelectric or thermal methods, or through a capacitive gate.

31. The device of claim 1, wherein the device is a frequency source.

32. The device of claim 1, wherein the device comprises a sensor.

33. The device of claim 1, wherein the device comprises an amplifier.

34. The device of claim 1, wherein the device comprises a neural network.

35. A method of using the device of claim 1, wherein the oscillators are used in a synchronized state.

36. The method of claim 35, further comprising:
synchronizing the oscillators;
applying a stimulus to the oscillators that modifies the oscillation of the oscillators:
combining output signals from the oscillators to generate a combined output signal indicative of the stimulus; and
outputting the combined output signal.

* * * * *